US012788356B2

(12) United States Patent
Xue et al.

(10) Patent No.: US 12,788,356 B2
(45) Date of Patent: Nov. 10, 2026

(54) METHOD AND SYSTEMS FOR RESPIRATORY SOUND CLASSIFICATION

(71) Applicant: NEWSOUTH INNOVATIONS PTY LIMITED, Sydney (AU)

(72) Inventors: Hao Xue, Melbourne (AU); Flora D. Salim, Melbourne (AU)

(73) Assignee: NEWSOUTH INNOVATIONS PTY LIMITED, Sydney (AU)

( * ) Notice: Subject to any disclaimer, the term of this patent is extended or adjusted under 35 U.S.C. 154(b) by 444 days.

(21) Appl. No.: 18/683,375

(22) PCT Filed: Aug. 15, 2022

(86) PCT No.: PCT/AU2022/050892

§ 371 (c)(1),
(2) Date: Feb. 13, 2024

(87) PCT Pub. No.: WO2023/015361

PCT Pub. Date: Feb. 16, 2023

(65) Prior Publication Data

US 2024/0341715 A1 Oct. 17, 2024

(30) Foreign Application Priority Data

Aug. 13, 2021 (AU) ................................ 2021902532

(51) Int. Cl.

| | |
|---|---|
| ***A61B 7/00*** | (2006.01) |
| ***A61B 5/00*** | (2006.01) |
| ***A61B 5/08*** | (2006.01) |

(52) U.S. Cl.

CPC ............ *A61B 7/003* (2013.01); *A61B 5/0816* (2013.01); *A61B 5/7267* (2013.01)

(58) Field of Classification Search

CPC ..... A61B 7/003; A61B 5/0816; A61B 5/7267; A61B 5/0823; A61B 5/08; G10L 25/66; G10L 25/30

(Continued)

(56) References Cited

U.S. PATENT DOCUMENTS 5,782,240 A * 7/1998 Raviv .................... A61B 7/003 600/529
2017/0076224 A1 3/2017 Munawar (Continued)

FOREIGN PATENT DOCUMENTS

DE 102008046285 A1 * 3/2010 ............. A61B 7/003
JP WO2016002004 A1 * 5/2017 ............. A61B 7/003
WO WO 2019229543 A1 * 12/2019 ............. A61B 7/003

OTHER PUBLICATIONS

International Search Report and Written Opinion in Application No. PCT/AU2022/050892, mailed Oct. 19, 2022, 19 pages.

(Continued)

*Primary Examiner* — Md I Uddin
(74) *Attorney, Agent, or Firm* — Meunier Carlin & Curfman LLC

(57) ABSTRACT

Described embodiments relate to methods, systems, and computer-readable media for training a feature encoder for encoding sound samples, such as respiratory sounds. Some embodiments further relate to methods, systems, and computer-readable media for training an audio classifier, such as a respiratory sound classifier, using the pre-trained feature encoder. Some embodiments relate to methods, systems, and computer-readable media for classifying a sample of an audio file, such as a respiratory sound, as being a positive example or a negative example of a condition, such as a respiratory condition.

17 Claims, 8 Drawing Sheets

(58) Field of Classification Search
USPC ........ 706/12, 15, 16, 18, 20, 21, 22, 25, 26, 706/44; 707/692, 694, 723, 736, 748, 707/754, 755, 756, 769, E17.014; 704/200, 239, 243, 245, 250, 258, 500, 704/503, E11.002
See application file for complete search history.

(56) References Cited

U.S. PATENT DOCUMENTS

| | | | | |
|---|---|---|---|---|
| 2018/0293510 | A1* | 10/2018 | Beigi | G06F 16/61 |
| 2020/0245873 | A1 | 8/2020 | Frank et al. | |
| 2022/0378377 | A1* | 12/2022 | Au | A61B 5/0205 |

OTHER PUBLICATIONS

Australian Search Report in Application No. 2021902832, mailed Dec. 24, 2021, 25 pages.
Xue, H. et al., 'Exploring Self-Supervised Representation Ensembles for COVID-19 Cough Classification', arXiv:2105.07566v2, Jun. 3, 2021.
Mendonça, J. et al., 'Using Self-Supervised Feature Extractors with Attention for Automatic COVID-19 Detection from Speech', arXiv:2107.00112vl, Jun. 30, 2021.
Song, W. et al., 'Contrastive Embeddind Learning Method for Respiratory Sound Classification', IEEE International Conference on Acoustics, Speech and Signal Processing (ICASSP), Canada, Jun. 6-11, 2021, 1275-1279.
Hoyos-Barceló, C. et al. 'Efficient computation of image moments for robust cough detection using smartphones', Computers inBiology and Medicine, vol. 100, 2018, 176-185.

* cited by examiner (a) Without Random Masking (b) With Random Masking

METHOD AND SYSTEMS FOR RESPIRATORY SOUND CLASSIFICATION

TECHNICAL FIELD

Embodiments generally relate to methods, systems, and computer-readable media for training a feature encoder for encoding sound samples, such as respiratory sounds. Some embodiments further relate to methods, systems, and computer-readable media for training an audio classifier, such as a respiratory sound classifier, using the pre-trained feature encoder. Some embodiments relate to methods, systems, and computer-readable media for classifying a sample of an audio file, such as a respiratory sound, as being a positive example or a negative example of a condition, such as a respiratory condition.

BACKGROUND

By Feb. 1, 2021, the total number of coronavirus disease 2019 (COVID-19) confirmed cases exceeded 103 million world-wide. Given that the global vaccination effort is still in its early stage, a practical and effective defensive procedure against the highly contagious COVID-19 is large-scale and timely testing, aimed at detecting and isolating the infected individuals as soon as possible.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

Some embodiments relate to a system comprising:

one or more processors; and memory comprising computer executable instructions, which when executed by the one or more processors, cause the system to:

a) determine a first training set comprising a plurality of audio files, wherein each audio file comprises a respiratory sound;

b) determine a database comprising a plurality of samples for each of the audio files of the first training set, wherein each sample is associated with an identifier;

c) determine a batch of sample pairs from the database, wherein the batch comprises one positive sample pair comprising a first sample and second sample, wherein the first sample and the second sample are associated with a common identifier, and the batch comprises a plurality of negative sample pairs, each negative sample pair comprising the first sample and a respective third sample, wherein the identifier associated with each respective third sample is different to the identifier associated with the first sample;

d) apply a first masking matrix having a first masking rate to the first sample to mask one or more select elements of the first sample in accordance with the first masking rate;

e) provide the masked first sample to a feature encoder to generate a first numerical representation of the masked first sample;

f) apply a second masking matrix having a second masking rate to the second sample to mask one or more select elements of the second sample in accordance with the second masking rate;

g) provide the masked second sample of the positive candidate pair to the feature encoder to generate a second numerical representation of the masked second sample;

h) provide the first numerical representation and the second numerical representation to a machine learning module to generate a first similarity measure indicative of the similarity between the masked first and second samples of the positive candidate pair;

i) determine a plurality of second similarity measures, each second similarity measure being indicative of the similarity between the first and third samples of each of the negative sample pairs, wherein said determining comprises:

for each negative sample pair:

i) apply a third masking matrix having a third masking rate to the third sample to mask one or more select elements of the third sample in accordance with the third masking rate;

ii) provide the masked third sample to the feature encoder to generate a third numerical representation of the masked third sample; and iii) provide the first numerical representation and the third numerical representation to the machine learning model to generate a second similarity measure between the first and third samples;

j) determine a loss function value using a loss function based on the first similarity measure, and the plurality of second similarity measures;

k) adjust one or more of the weights of the feature encoder based on the determined loss function value;

l) responsive to a iteration count being less than a threshold value:

i) increment the iteration count; and ii) repeat c) to k);

m) responsive to the iteration count reaching the threshold value, determine the feature encoder as a pre-trained feature encoder.

In some embodiments, the computer executable instructions, which when executed by the one or more processors, further cause the system to:

a) determine a second training set of a plurality of audio files, each audio file comprising a label indicative of whether the sound is a positive example of a condition or a negative example of the condition;

b) generate a batch of samples from the second training set, wherein each sample is generated from a respective audio file and is associated with the label of the audio file from which it was generated; and c) for each of the plurality of samples of the second batch:

i) select a candidate sample from the second batch;

ii) provide the candidate sample to the pre-trained feature encoder to generate a candidate numerical representation of the candidate sample;

iii) provide the candidate numerical representation to a classifier to determine a predictive score, wherein the predictive score is indicative of the likelihood of the candidate sample being a positive example of the condition; and iv) adjust one or more weights of the classifier based on the label associated with the candidate sample and the predictive score.

In some embodiments, the pre-trained feature encoder comprises a first pre-trained feature encoder and a second pre-trained feature encoder, and wherein the computer executable instructions, which when executed by the one or more processors, cause the system to provide the candidate sample to the pre-trained feature encoder further cause the system to:

a) apply a fourth masking matrix having a fourth masking rate to the candidate sample to mask one or more select elements of the candidate sample in accordance with the fourth masking rate to provide a fourth masked sample;
b) apply a fifth masking matrix having a fifth masking rate to the candidate sample to mask one or more select elements of the candidate sample in accordance with the fifth masking rate to provide a fifth masked sample; and
c) provide the fourth masked sample to the first pre-trained encoder to generate a fourth numerical representation of the fourth masked sample and providing the fifth masked sample to the second pre-trained encoder to generate a fifth numerical representation of the fifth masked sample; and wherein providing the candidate numerical representation to the classifier comprises providing both the fourth numerical representation and the fifth numerical representation as inputs to the classifier.

Some embodiments relate to a computing device comprising:

one or more processors; and memory comprising computer executable instructions, which when executed by the one or more processors, cause the computing device to:

determine an audio file comprising a respiratory sound;

provide a sample of the audio file to a respiratory sound classification module, wherein the respiratory sound classification model was trained using a contrastive pre-trained feature encoder; and determine an output from the respiratory sound classification module, wherein the output in indicative of whether or not the respiratory sound is a positive or negative example of a respiratory condition.

In some embodiments, providing the sample of the audio file to the respiratory sound classification module further causes the system to:

a) mask the sample using a masking matrix with an associated masking rate; and
b) provide the masked sample to the cough classification module.

The computing device is a mobile phone device or a smart sensor. The respiratory sound classification module may be a cough classification module.

Some embodiments relate to a method comprising:

a) determining a first training set comprising a plurality of audio files, wherein each audio file comprises a respiratory sound;
b) determining a database comprising a plurality of samples for each of the audio files of the first training set, wherein each sample is associated with an identifier;
c) determining a batch of sample pairs from the database, wherein the batch comprises one positive sample pair comprising a first sample and second sample, wherein the first sample and the second sample are associated with a common identifier, and the batch comprises a plurality of negative sample pairs, each negative sample pair comprising the first sample and a respective third sample, wherein the identifier associated with each respective third sample is different to the identifier associated with the first sample;
d) applying a first masking matrix having a first masking rate to the first sample to mask one or more select elements of the first sample in accordance with the first masking rate;
e) providing the masked first sample to a feature encoder to generate a first numerical representation of the masked first sample;
f) applying a second masking matrix having a second masking rate to the second sample to mask one or more select elements of the second sample in accordance with the second masking rate;
g) providing the masked second sample of the positive candidate pair to the feature encoder to generate a second numerical representation of the masked second sample;
h) providing the first numerical representation and the second numerical representation to a machine learning module to generate a first similarity measure indicative of the similarity between the masked first and second samples of the positive candidate pair;
i) determining a plurality of second similarity measures, each second similarity measure being indicative of the similarity between the first and third samples of each of the negative sample pairs, wherein said determining comprises:

for each negative sample pair:

i) applying a third masking matrix having a third masking rate to the third sample to mask one or more select elements of the third sample in accordance with the third masking rate;
ii) providing the masked third sample to the feature encoder to generate a third numerical representation of the masked third sample; and
iii) providing the first numerical representation and the third numerical representation to the machine learning model to generate a second similarity measure between the first and third samples;

j) determining a loss function value using a loss function based on the first similarity measure, and the plurality of second similarity measures;
k) adjusting one or more of the weights of the feature encoder based on the determined loss function value;
l) responsive to a iteration count being less than a threshold value:
   i) incrementing the iteration count; and
   ii) repeating steps c) to k); and
l) responsive to the iteration count reaching the threshold value, determining the feature encoder as a pre-trained feature encoder.

In some embodiments, the method further comprises:

a) determining a second training set of a plurality of audio files, each audio file comprising a label indicative of whether the sound is a positive example of a condition or a negative example of the condition;
b) generating a batch of samples from the second training set, wherein each sample is generated from a respective audio file and is associated with the label of the audio file from which it was generated; and
c) for each of the plurality of samples of the second batch:
   i) selecting a candidate sample from the second batch;
   ii) providing the candidate sample to the pre-trained feature encoder to generate a candidate numerical representation of the candidate sample;

iii) providing the candidate numerical representation to a classifier to determine a predictive score, wherein the predictive score is indicative of the likelihood of the candidate sample being a positive example of the condition; and iv) adjusting one or more weights of the classifier based on the label associated with the candidate sample and the predictive score.

The pre-trained feature encoder may comprise a first pre-trained feature encoder and a second pre-trained feature encoder, and providing the candidate sample to the pre-trained feature encoder may comprise:

a) applying a fourth masking matrix having a fourth masking rate to the candidate sample to mask one or more select elements of the candidate sample in accordance with the fourth masking rate to provide a fourth masked sample;

b) applying a fifth masking matrix having a fifth masking rate to the candidate sample to mask one or more select elements of the candidate sample in accordance with the fifth masking rate to provide a fifth masked sample; and c) providing the fourth masked sample to the first pre-trained encoder to generate a fourth numerical representation of the fourth masked sample and providing the fifth masked sample to the second pre-trained encoder to generate a fifth numerical representation of the fifth masked sample; and wherein providing the candidate numerical representation to the classifier comprises providing both the fourth numerical representation and the fifth numerical representation as inputs to the classifier.

The first and second pre-trained feature encoders may be initialized using: (i) the same pre-trained weights; or (ii) different pre-trained weights.

In some embodiments, the pre-trained feature encoder comprises a third pre-trained feature encoder and wherein providing the candidate sample to the pre-trained feature encoder comprises:

a) applying a sixth masking matrix having a sixth masking rate to the candidate sample to mask one or more select elements of the candidate sample in accordance with the sixth masking rate to provide a sixth masked sample;

b) providing the sixth masked sample to the first pre-trained encoder to generate a sixth numerical representation of the sixth masked sample; and wherein providing the candidate numerical representation to the classifier further comprises providing the sixth numerical representation as an input to the classifier.

The fourth and/or fifth sampling matrices may be generated using a pseudo-random number generator. The first and/or second and/or third sampling matrices may be generated using a pseudo-random number generator.

In some embodiments, determining the database comprising the plurality of samples comprises:

i) transforming each audio file into a feature matrix, each feature matrix comprising a first dimension corresponding to a number of frequency bins, and a second dimension corresponding to a number of time frames in the audio file;

ii) for each feature matrix, generating at least one sample, each sample comprising the first dimension corresponding to a number of frequency bins, and a third dimension corresponding to a predefined number of time frames, wherein the third dimension is a subset of the second dimension. Each of the plurality of samples may comprise at least a portion of a sound of a respective audio file.

The feature encoder may be a Transformer based feature encoder. The feature encoder may be a Convolutional Neural Network (CNN) based feature encoder. The feature encoder may be a Recurrent Neural Network (RNN) based feature encoder.

The machine learning model may generate a similarity measure using one of: (i) a cosine similarity metric; and (ii) a bilinear similarity metric.

In some embodiments, each audio file of the first training set comprises a respiratory sound. In some embodiments, each audio file of the second training set comprises a respiratory sound. The respiratory sound may be a cough. The condition may be a respiratory condition. The respiratory condition may be a classification of a cough. The respiratory condition may be COVID-19.

In some embodiments, the audio files of the first training set do not include labels indicative of whether the sound of the audio file is a positive example of a condition or a negative example of the condition.

In some embodiments, the trained feature encoder and the trained classifier on a computing device for use.

Some embodiments relate to a method comprising:

a) determining an audio file comprising a respiratory sound;

b) providing a sample of the audio file to a respiratory condition classification module, wherein the respiratory condition classification model was trained using a contrastive pre-trained feature encoder; and c) determining an output from the respiratory condition classification module, wherein the output in indicative of whether or not the respiratory sound is a positive or negative example of a respiratory condition. For example, the respiratory condition classification module may be a cough classification module.

In some embodiments, providing the sample of the audio file to the cough classification module further comprises:

a) masking using a masking matrix with an associated masking rate; and b) providing the masked sample to the cough classification module.

In some embodiments, the output is provided to a user, for example, via a user interface.

In some embodiments, the respiratory condition or cough classification module is trained according to any one of the described methods.

Some embodiments relate to a system comprising:

one or more processors; and memory comprising computer executable instructions, which when executed by the one or more processors, cause the system to perform any one of the described methods.

Some embodiments relate to a computer-readable storage medium storing instructions that, when executed by a computer, cause the computer to perform any one of the described methods.

Some embodiments relate to a computing device comprising:

one or more processors; and memory comprising computer executable instructions, which when executed by the one or more processors, cause the computing device to perform any one of the described methods.

In some embodiments, memory of the computing device comprises a trained respiratory condition or cough classification module.

In some embodiments, the respiratory condition or cough classification module has been trained according to any one of the described methods.

In some embodiments, the computing device is a mobile phone device or a smart sensor.

Some embodiments relate to computer-readable media storage medium storing instructions that, when executed by a computer, cause the computer to perform any one of the described methods.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Various ones of the appended drawings merely illustrate example embodiments of the present disclosure and cannot be considered as limiting its scope.

DESCRIPTION OF EMBODIMENTS

Embodiments generally relate to methods, systems, and computer-readable media for training a feature encoder for encoding sound samples, such as respiratory sounds. Some embodiments further relate to methods, systems, and computer-readable media for training a sound classifier, such as a respiratory sounds classifier, using the pre-trained feature encoder. Some embodiments relate to methods, systems, and computer-readable media for classifying a sample of an audio file, such as a respiratory sound, as being a positive example or a negative example of a condition, such as a respiratory condition.

Described embodiments may provide for a reliable, readily-accessible, and/or contactless approach for preliminary diagnosis of respiratory conditions, such as COVID-19. This can be of particular benefit in regions where medical supplies/workers and personal protective equipment are limited.

Cough is one of the major symptoms of COVID-19 patients. Compared to PCR (Polymerase Chain Reaction) tests and radiological images, diagnosis using cough sounds can be readily accessed by people using a computing device such as a smartphone. However, cough is also a common symptom of many other medical conditions that are not related to COVID-19. Therefore, automatically classifying respiratory sounds for a specific respiratory condition, such as COVID-19 diagnostic, is a non-trivial and challenging task.

Figure 1:
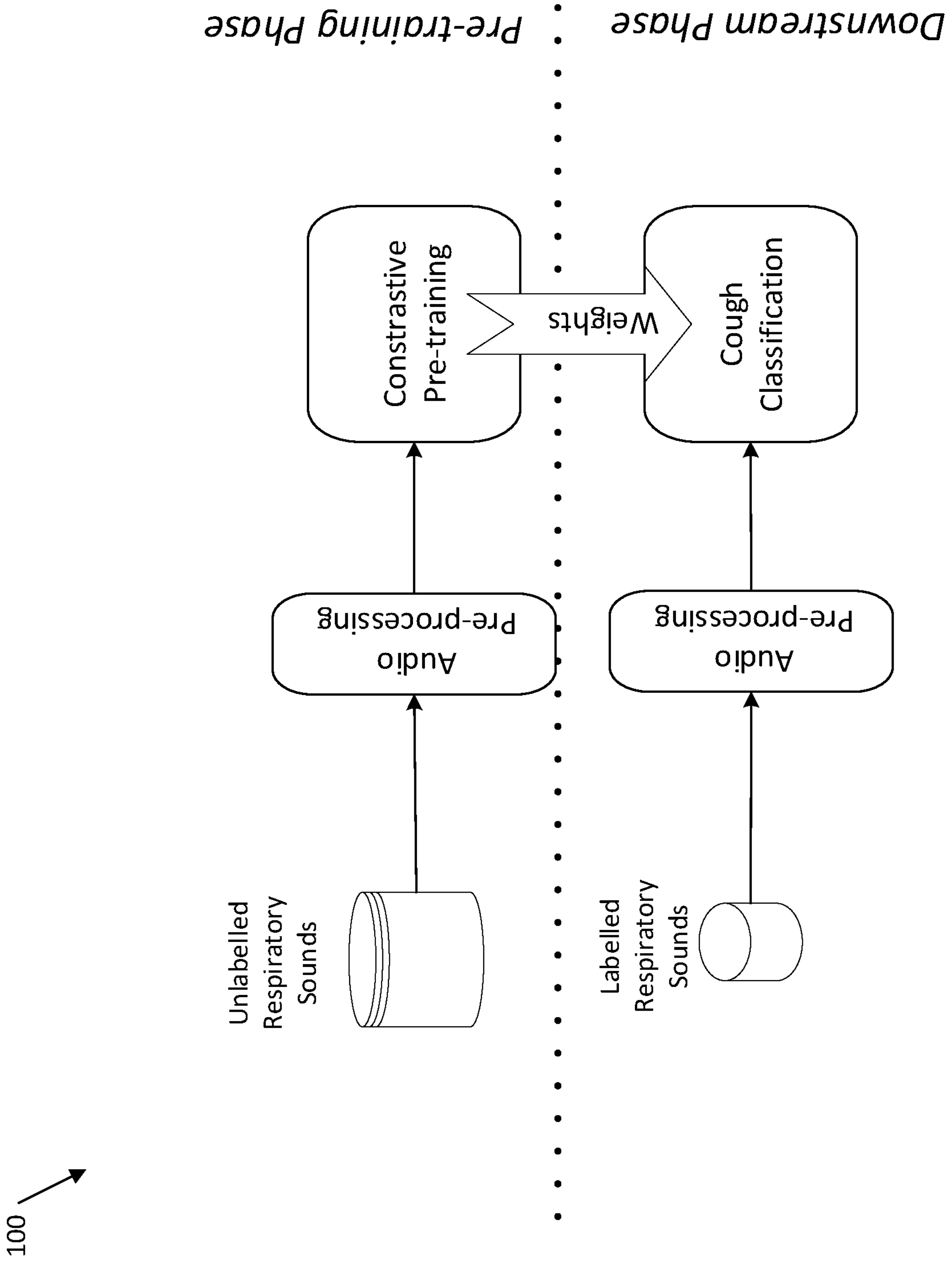
FIG. 1 is a schematic overview of an example process for training a sound classification model, according to some embodiments.

Described embodiments relate to a self-supervised learning enabled framework for respiratory sound, such as cough, classification. The described embodiments comprise a two-phase framework, as illustrated in the schematic of FIG. 1. The first phase is a contrastive pre-training phase for training a feature-based encoder, such as a Transformer-based feature encoder, using unlabelled audio data or audio data that need not be labelled; that is labels indicative of the health condition of the individual associated with each example of audio data are not required for this phase of the training (whether present or not). In some embodiments, a random masking mechanism is used to learn robust numerical representations of respiratory sounds. A purpose of the first phase is to train a feature encoder contrastively so that it can learn discriminative representations from large amount of unlabelled sounds. The first phase provides a pre-trained feature encode configured to provide effective and general representations, which may boost the classification performance in the second (downstream) phase.

The second phase involves using the pre-trained feature encoder in conjunction with a classifier to perform respiratory sound (e.g. cough) classification. During this phase, labelled data is used to train the classifier. The weights of the contrastive pre-trained feature encoder transferred from the first phase may be fine-tuned based on the labelled dataset. In some embodiments of the second phase, multiple instances of the pre-trained feature encoder (different ensembles) with varied masking rates are provided.

Evaluations on the described embodiments as discussed in further detail below demonstrate the effectiveness of the described contrastive pre-training, the random masking mechanism, and the ensemble architecture in providing improved respiratory sound classification performance.

This approach differs from that of designing training a classifier in a fully fully-supervised way and addresses some of the limitations of such an approach. A fully-supervised approach limits the applicability, effectiveness and impact of the collected datasets, since the classifier is trained and tested on the same dataset. This means additional datasets can-not be directly used to boost the predictive performance of the classifier; it is limited to the same source dataset. Further, such fully-supervised based classification training methods would tend to need to rely on well-annotated (labelled) respiratory sound data. For example, the annotations or labels may be provided by experts or user response surveys. There are two inherent limitations of these annotation approaches: (i) Annotation Cost: Annotation of a large-scale dataset generally comes at an expensive cost (both financial cost and human power cost). In addition, unlike the data labelling in other tasks such as image classification, the annotation of respiratory sounds tends to require specific knowledge from experts. This further aggravates the difficulty of obtaining accurate annotations. (ii) Privacy Concern: Although directly asking participants to report their health status (e.g., whether the COVID-19 is tested positive or negative) during the respiratory sounds collection avoids annotation cost, the medical information is highly sensitive. Such privacy concerns also limit the distribution and publicity of gathered datasets. For example, some datasets have to be accessed by one-to-one legal agreements and specific licenses.

Described embodiments leverage large scale unlabelled respiratory sounds to improve the performance of respiratory condition classification. For example, the described embodiments can take advantage of unlabelled respiratory sounds to reduce the annotation dependency in the training process of the classifier.

Respiratory sound classification modules trained according to the described embodiments may be deployed on computing devices, such as smart phones or smart sensors to perform respiratory classification locally. In some embodiments, applications deployed on computing devices, such as smart phones or smart sensors, may be configured to capture audio files, or samples, indicative of a respiratory sound of an individual, and to transmit the audio file or sample to a system or server, such as a remote server whereon the respiratory sound classification module is deployed, and to receive a response from the system or server indicative of the output of the respiratory sound classification module, i.e., positive or negative for a particular respiratory condition.

Figure 2:
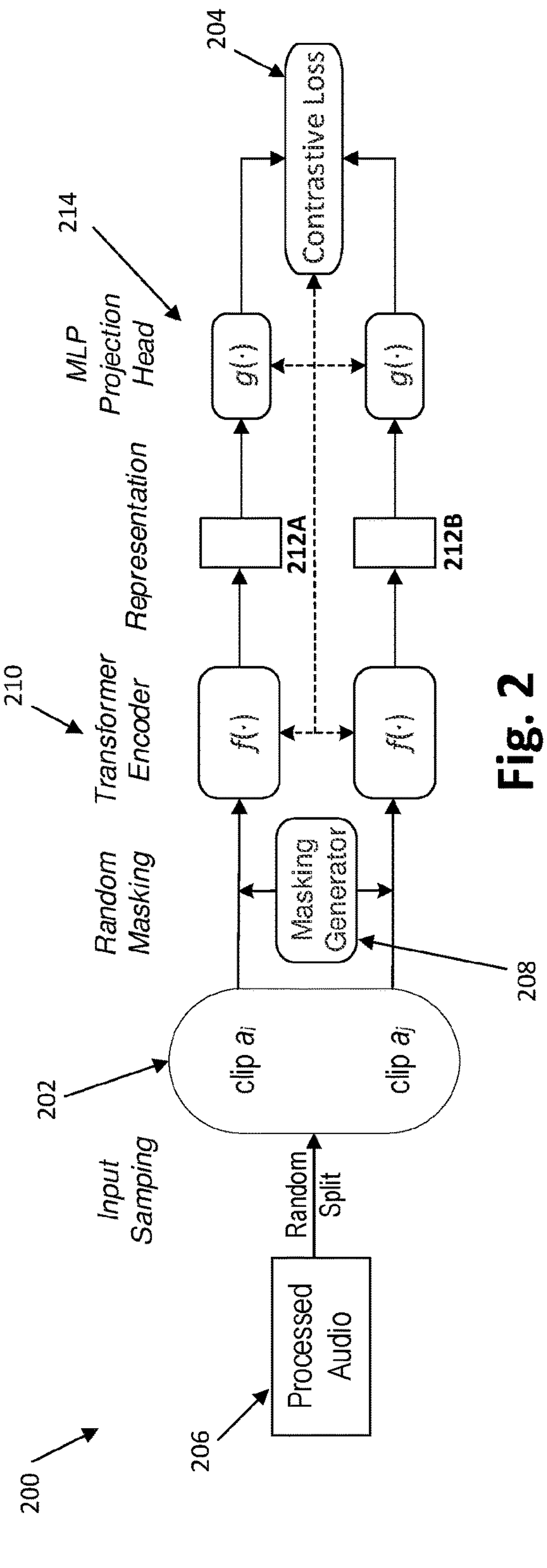
FIG. 2 is a block diagram of a pipeline for training a feature encoder for sounds, according to some embodiments.

Referring now to FIG. 2, there is shown a block diagram of a pipeline of a system 200 for contrastive pre-training of a feature encoder for audio, such as respiratory sounds, according to some embodiments.

A sample pair 202 of pre-processed audio or sound samples is provided as an input to the pipeline and a similarity measure based on a contrastive loss function 204 is provided as an output. The similarity measure is indicative of the similarity of the samples of the sample pair to one another. In other words, the system 200 is configured to encode audio samples into a latent space using a feature encoder so that the similarity of positive samples if larger than the negative samples in the latent space.

The samples are derived from audio files 206, pre-processed to generate one or more feature matrices from which the audio samples or clips are generated. Prior to selection of the audio files, the audio files may be filtered to remove audio files that are silent and/or too noisy. Pre-processing is performed to read and transform each audio file into a matrix format suitable for providing as an input to a feature encoder, such as feature encoder 210. In some embodiments, Mel Frequency Cepstral Coefficients (MFCC) or log-compressed mel-filterbanks may be used to generate the matrix format of the audio files, For example, the Python Speech Features package8 may be used for computing log-compressed mel-filterbanks. After such preprocessing, each raw audio file is mapped to a feature matrix $a \in \mathbb{R}^{N \times T}$, where N is a number of frequency bins and T is a total number of time frames in the audio file. Since different audio files in a dataset may have different lengths and/or different T values after pre-processing, a sliding window with window size Tw may be applied to generate multiple samples for each processed audio file.

If sample i: $a_i \in \mathbb{R}^{N \times T_w}$, and sample j: $a_j \in \mathbb{R}^{N \times T_w}$ are derived or sampled from the same audio clip, they are considered to be a positive pair, but if they are derived or sampled from different audio files, they may be considered a negative pair. In some embodiments, samples derived from different audio files may be considered a positive pair if the different audio files are of or associated with the same individual. For example, if they are both examples of a respiratory sound of or from the same person. It may be the case that the database includes four audio files from the same individual or participant—for example, fast/slow breathing and deep/shallow cough sounds. If two samples are from the same participant, they may be considered as being a positive pair. Generally, after contrasting learning, samples from the same person have a larger similarity in the latent space than samples from different people. In this phase, there is no requirement for audio files or samples to include any labels indicative of the health condition, such as respiratory condition, of the individual.

System 200 comprises a masking generator 208 for generating masking matrices with particular masking rates. The generated masking matrix is configured to have a dimension of the sample to which it is to be applied. The masking rate is a percentage of the time steps of the sample to be masked. In some embodiments, the masking matrix is pseudo randomly generated according to the masking rate such that of the time steps of the sample to be masked are pseudo randomly selected. For example, the masking generator 208 may generate a masking matrix with a masking rate of 60% where a first second and third time step (of a five time step sample) are masked and the fourth and fifth time step are not masked. The masking generator 208 may also generate a masking matrix with a masking rate of 60% where a second, fourth and fifth time step (of a five time step sample) are masked and the first and second time step are not masked. Masking elements or time steps of a sample means that the masked one or more elements of the masked sample are removed from an attention calculation of the feature encoder.

In some embodiments, the masking generator 208 is provided to generate a first masking matrix with a first masking rate and a second masking matrix with a second masking rate. The first masking matrix with a first masking rate is applied to a first sample of the sample pair, and the second masking matrix with the second masking rate is applied second sample of the sample pair. In some embodiments, the masking generator 208 used a pseudo random number generator to generate pseudo random masks and/or masking rates; in other words, the masking generated randomly generates the masking matrices with the specific masking rates. The masking rates are adjustable hyper-parameters. The first and second masking rates may be the same or different from one another. Based on the masking matrix and the masking rate, select inputs are masked, and in some embodiments, randomly masked, and removed from an attention calculation of the feature encoder 210, as discussed in more detail below with reference to FIGS. 3(*a*) and 3(*b*).

The masked samples are provided to a feature encoder 210 to generate first and second numerical representations of the respective first and second samples, 212A and 212B. The goal of the feature encoder 210 is to embed each sample, $a_i \in \mathbb{R}^{N \times T_w}$, into a representation vector, $h_i \in \mathbb{R}^d$, where d the dimension of a representation vector. This step may be formulated as:

$$h_i = f(a_i, M_i; W_f),$$

where f (•) represents the feature encoder 210, $W_f$ are trainable weights of the feature encoder 210, and $M_i$ is the masking matrix for sample at. Similarly, $h_j \in \mathbb{R}^d$ for sample $a_j$ is obtained.

Figure 3A:
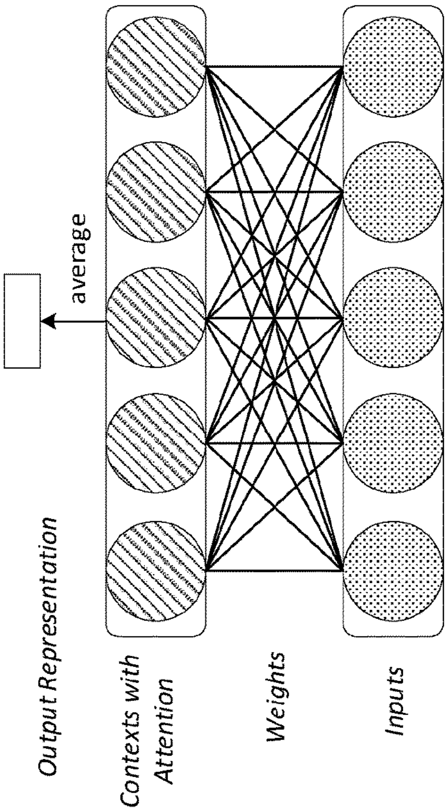
FIGS. 3(*a*) and 3(*b*) are schematics depicting the application of unmasked inputs to the feature encoder of FIG. 2, and the application of masked inputs to the feature encoder of FIG. 2.
Figure 3B:
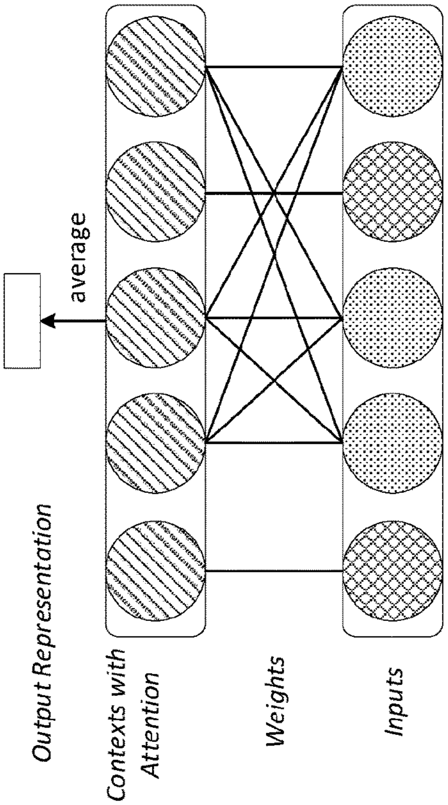

In some embodiments, a Transformer structure is selected as the encoder f (•). As shown in FIG. 3(*a*), the typical Transformer structure models an input sequence through an attention mechanism; $a_i$ is considered as a $T_W$ time steps sequence and each time step is N dimensional. For each time step, the scaled dot-product attention for every other time step is calculated. However, such a densely calculated attention mechanism may cause over-fitting to the dataset used for training in this phase. Additionally, where the samples comprise respiratory sounds or similar, a feature at each time step may not always be meaningful; a collected audio file often contains noises such as a short pause between coughs. Accordingly, some features of samples may be relatively meaningless. To compensate for such situations, and with a view to making the pre-trained feature encoder 210 more robust, the masking mechanism is used, as illustrated in FIG. 3(*b*). In FIG. 3(*b*), the first and fourth inputs are masked and removed from the attention calculation of the feature encoder 210. Accordingly, and although a masked time step of a sample is passed through to a next layer of the feature encoder 210, the scaled dot-product attention for every other time step is not calculated for a masked time step. For example, with a 40% masking rate, 2 time steps (the first and fourth of FIG. 3(*b*)) out of the five time steps are masked and removed from the attention mechanism of the feature encoder 210.

The first and second numerical representations, 212A and 212B are provided to a machine learning program or module 214 to determine a loss function value indicative of the similarity measure between the two samples.

The system 200 is configured to train the machine learning module 214 and the feature encoder 210 by contrastive learning. The machine learning module 214 comprises a projection head (•), which is applied to map the numerical representations 212A and 212B of the sample pair to the latent space where the similarity measure is determined.

In some embodiments, a cosine similarity metric is used, and the similarity of a sample pair is given by:

$$sim(a_i, a_j) = \frac{g(h_i)^\top \cdot g(h_j)}{\|g(h_i)\|\|g(h_j)\|}$$

In some embodiments, a bilinear similarity metric is used, and the similarity of a sample pair is given by:

$sim(a_i,a_j)=g(h_i)^T W_s g(h_j)$, where $W_s$ is a bilinear parameter.

The performance of the Cosine similarity metric and the bilinear similarity metric is discussed in more detail below.

The loss function for contrastive learning used in the pre-training phase of system 200 may be a multi-class cross-entropy function working with the similarity metric. During the training in this phase, each training instance involves a pair of samples. Each training batch may comprise a positive pair and a plurality of negative pairs. Two samples derived from the same audio file and/or from the same individual constitute a positive pair, and two samples derived from different audio files and/or different individuals constitute a negative pair. Each training instance may be considered as a unique class, and accordingly, multi-class cross0entropy may be applied. The loss function is calculated over the batch; the batch has size B, with 2B samples per batch. In some embodiments, the loss function may be calculated as:

$$\mathcal{L}_{contrastive} = -\log\frac{\exp\left(\frac{sim(a_i, a_j)}{\tau}\right)}{\sum_{k=1}^{2B}\exp\left(\frac{sim(a_i, a_j)}{\tau}\right)}, k \neq i$$

where τ denotes the temperature parameter for scaling, $a_i$ and $a_j$ are the positive pair, and $a_i$ and $a_k$ ((k≠i) are the negative pairs.

Weights of the machine learning program or module 214 and the feature encoder 210 may be adjusted based on the loss function value by way of backward propagation to thereby train the machine learning program or module 214 and the feature encoder 210 to provide an improved performance.

As described below with reference to method 600 of FIG. 6, the feature encoder 210 can be trained to generate numerical representations of sound samples that allow for improved distinction between similar sounds and dissimilar sounds. The trained feature encoder 210 may then be used in a subsequent phase to train a classifier (410 of FIG. 4) to classify a sound as being a positive or a negative example of a particular condition, such as a respiratory condition.

Figure 4:
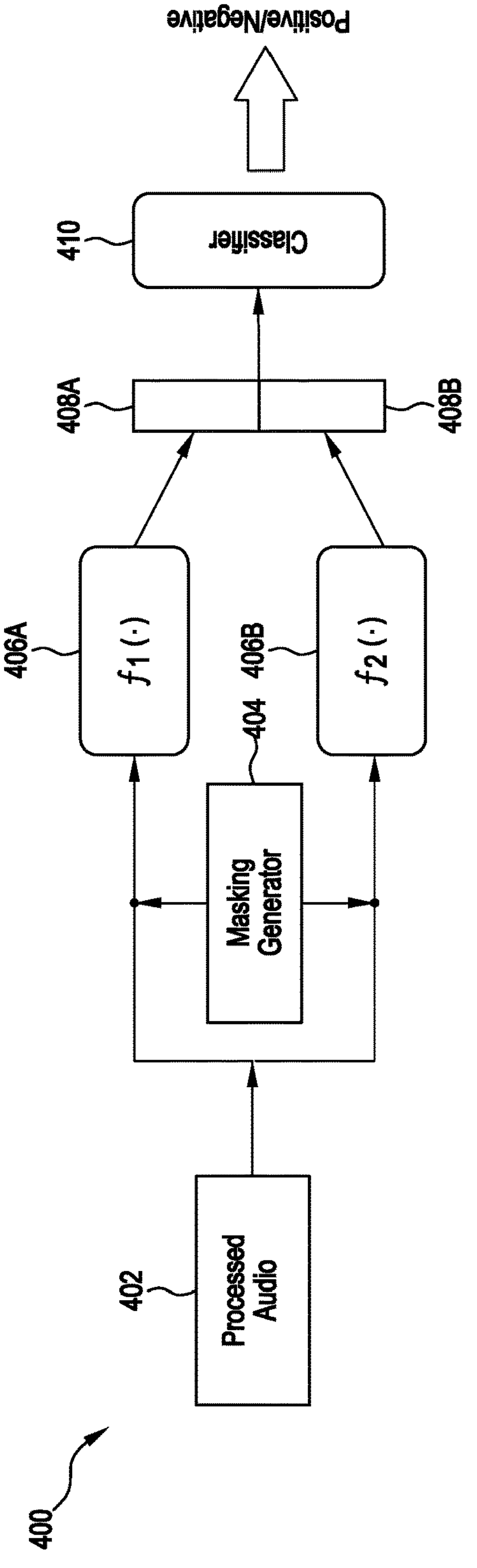
FIG. 4 is a block diagram of a pipeline for training a classifier using the trained feature encoder of FIG. 2, according to some embodiments.

Referring to FIG. 4, there is a block diagram of a pipeline of a system 400 for training a classifier using the pre-trained feature encoder 210 of FIG. 2, according to some embodiments. In some embodiments, the system 400 is fine-tuned with labelled data end-to-end with typical binary cross-entropy classification loss.

As an input to the pipeline 400, a candidate sample is selected from a training set of processed audio 402 and provided for each training iteration. The samples of the training set are each derived or sampled from an audio file in a manner similar to that of the pre-processing of the audio files described above in relation to FIG. 2. However, each of the audio files from which the samples are derived is associated with a label indicative of whether the sound of the audio file is a positive example of a condition or a negative example of a health condition. For example, the sound may be a respiratory sound, such as a cough, and the condition may be a respiratory condition, such as COVID-19. Further, each sample is likewise associated or labelled with the label of the audio file from which it was generated.

A masking generator 404 generates a first masking matrix having a first masking rate and a second masking matrix having a second masking rate. The first masking matrix with the first masking rate is applied to the candidate sample to generate a first masked candidate sample, and the second masking matrix with the second masking rate is applied to the candidate sample to generate a second masked candidate sample. In this way, two separate branches of input to the feature encoder(s) are generated.

In some embodiments, the first and second masked candidate samples are provided to a first and second instance of the pre-trained feature encoder 210, 406A and 406B, respectively; that is, the feature encoder pre-trained in accordance with the pipeline of FIG. 2. In other words, the system 400 comprises an ensemble structure or architecture for the feature encoder. Both instances of the pre-trained feature encoder 406A and 406B may be initialized with the same pre-trained weights as determined in the pre-training phase of performed by the system 200 of FIG. 2. In other embodime In some embodiments, the first and second masking matrices applied to the candidate sample are generated randomly. Accordingly, the two branches of masked candidate samples provided to the ensemble structure of feature encoders may have different masked time steps. This means that the two instances of the feature encoders 406A and 406B may model their inputs and yield encoded features from a different perspective. Thus, the ensemble structure and the random masking mechanism is a harmonized match and beneficial to each other.

In some embodiments, the ensemble structure may comprise two pre-trained feature encoders 210. In some embodiments, the ensemble structure may comprise three or more feature encoders 210. The two or more feature encoders 210 of the ensemble structure may be multiple instances of the same pre-trained encoder 210; in other words, each feature encoder of the ensemble structure may be initialised using the same pre-trained weights. In some embodiments, the ensemble structure may comprise multiple pre-trained feature encoders 210, wherein at least two of the pre-trained feature encoders were pre-trained independently of one another and are initialized using different pre-trained weights. The first and second instances of the pre-trained feature encoder 210 generate first and second numerical representations, 408A and 408B, of the first and second sampled candidate samples, respectively.

The first and second numerical representations are then provided as inputs to a classifier 410 to determine a predictive score. Unlike a more straightforward architecture, the classifier 410 has 2d input neurons as it takes the concatenated feature as input; in other words, the concatenation of two encoded features from the pre-trained feature encoder 406A and 406B, respectively.

The predictive score may be indicative of the likelihood of the candidate sample being a positive example of the condition. For example, if the probability is greater than a threshold, such as 0.5, the sample is considered to be a positive example, and vice versa.

In some embodiments, the classifier 410 may be is a fully connected layer with d (feature dimension of the encoded feature $h_i$) input neurons and one output node with sigmoid activation function to output the probability and indicate whether the input sound sample For example, the classifier may output the probability that the input respiratory sound sample is COVID-19 positive (probability larger than a threshold, e.g. 0.5) or negative (probability smaller than the threshold).

The determined predictive score and the label associated with the candidate sample may be used to adjust one or more weights of the classifier 410 and/or one or more weights of the instances of the pre-trained feature encoder 406A and 406B to more accurately train the classifier 410 and/or the pre-trained feature encoders 406A and 406B. For example, the label may be used as a measure of how accurate the predictive score for the sample was. In some embodiments, the pre-trained feature encoder 406A and 406B may be updated differently.

By using an ensemble structure comprises at least two pre-trained feature encoders, the robustness and the reliability of the feature encoder 210 and/or classifier 410 may be improved. This may be due to the averaging of the two of more branches associated with the outputs of the pre-trained feature encoders. For example, assume that a sample has a five time-step and the most distinguishable feature is on the second time-step. With only one branch (one feature encoder 210), this feature might be missed due to the random masking. However, with the two-branch design, this feature would have a higher chance of being captured by the feature encoder 210.

Figure 6:
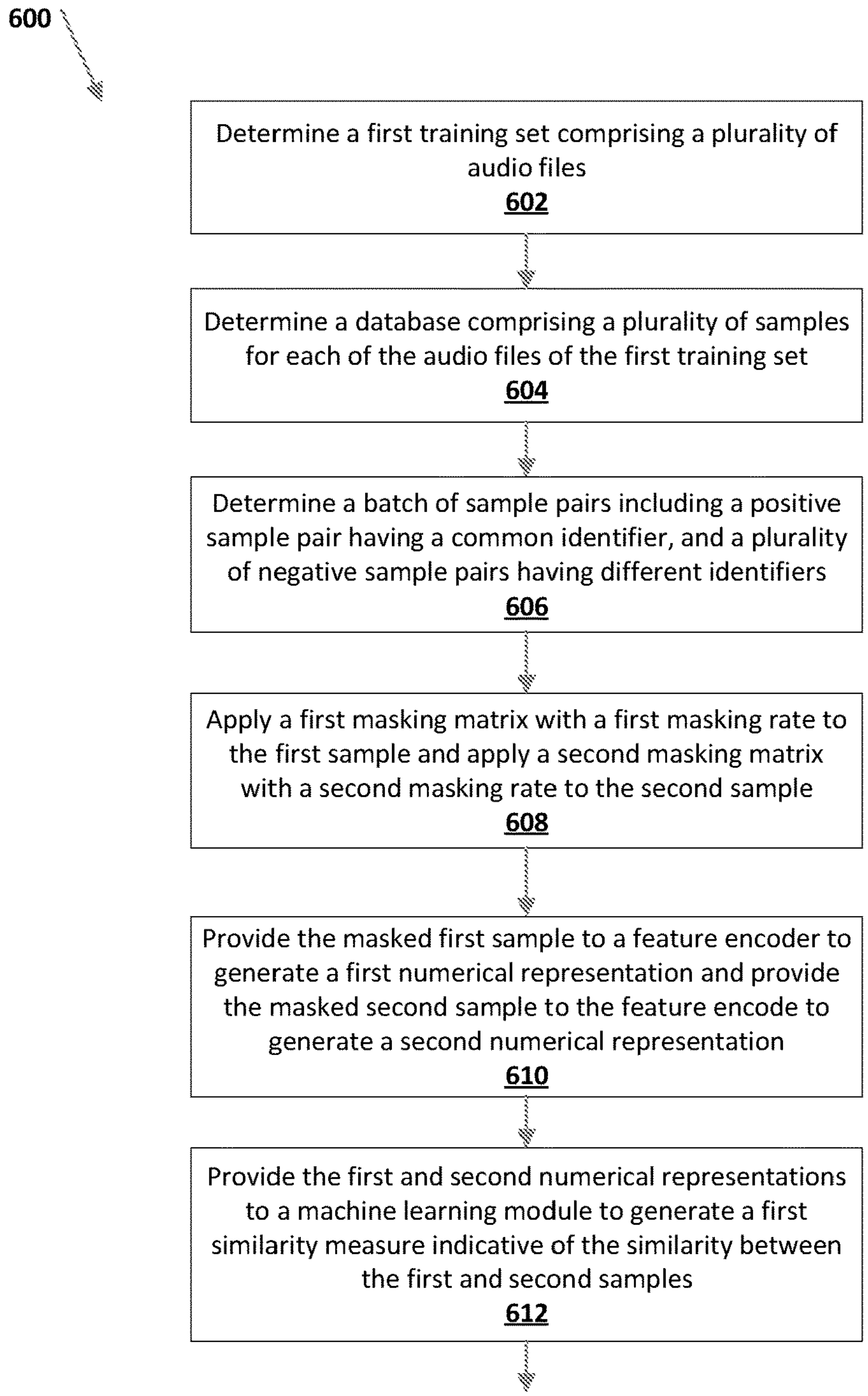
FIG. 6 is a process flow diagram of a method of training a feature encoder for sounds, according to some embodiments.
Figure 6:
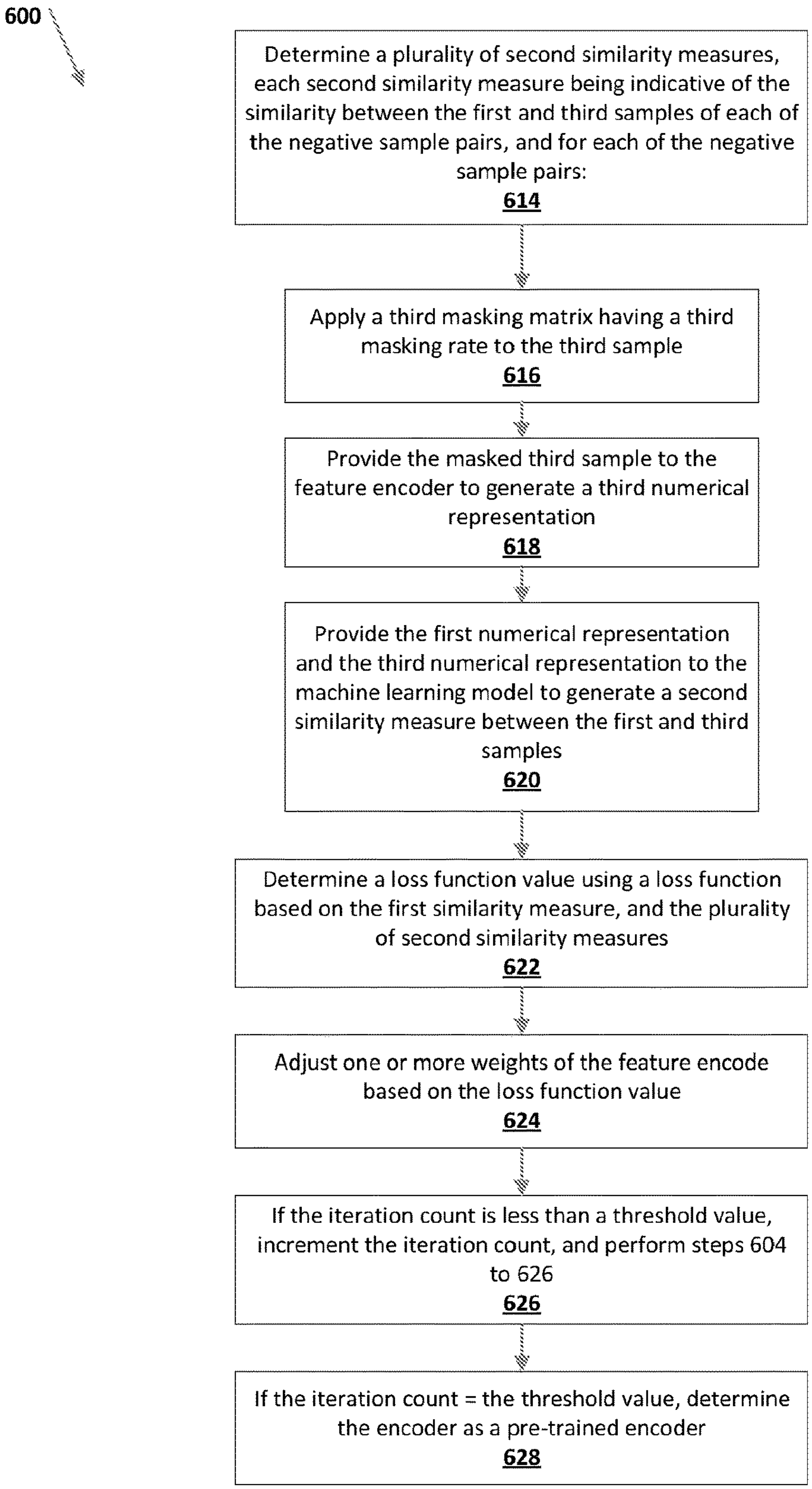

FIG. 6 is a process flow diagram of a method 600 for training a feature encoder, according to some embodiment. The method 600 may, for example, be performed by processor(s) 910 of system 902 executing the modules and/or models stored in memory 912, as discussed in further detail below with reference to FIG. 9.

At 602, the system 902 determines a first training set comprising a plurality of audio files. In some embodiments, the audio files of the first training set may not include labels indicative of whether the sound of the audio file is a positive example of a condition or a negative example of a particular condition. In embodiments where at least some of the audio files of the first training set include labels indicative of whether the sound of the audio file is a positive or negative example of a particular condition, those label are not used or required for the purposes of performing the method 600; in other words, the method involves a contrastive approach to pre-training a feature encoder 916 for audio or sound samples, such as respiratory sounds.

In some embodiments, each audio file of the first training set comprises a respiratory sound, such as a cough. In some embodiments, the condition is a respiratory condition, or a classification of a cough, such as COVID-19.

At 604, the system 902 determines a database 904 comprising a plurality of samples for each of the audio files of the first training set. Each sample may be associated with an identifier. The identifier may be indicative of the audio file from which the sample was derived and/or may be indicative of a person associated with the sound of the audio file, for example, the person the sound, such as a respiratory sound, was made by.

In some embodiments, determining the database 904 comprising the plurality of samples comprises transforming each audio file into a feature matrix. In some embodiments, pre-processing techniques such as Mel Frequency Cepstral Coefficient (MFCC) or log-compressed mel-filterbanks are used to transform audio signals into 2D matrices.

For example, each feature matrix may comprise a first dimension corresponding to a number of frequency bins, and a second dimension corresponding to a number of time frames in the audio file. The system may, for each feature matrix, generate at least one sample. Each sample may comprise the first dimension corresponding to a number of frequency bins, and a third dimension corresponding to a predefined number of time frames. The third dimension may be a subset of the second dimension. Each of the plurality of samples may comprises at least a portion of a sound of a respective audio file.

At 606, the system 902 may determine a batch of sample pairs including a positive sample pair having a common identifier, and a plurality of negative sample pairs having different identifiers. For example, the batch may comprise one positive sample pair comprising a first sample and second sample. The first sample and the second sample may be associated with a common identifier. The batch may comprise a plurality of negative sample pairs, and each negative sample pair may comprise the first sample and a respective third sample, wherein the identifier associated with each respective third sample is different to the identifier associated with the first sample. Selection and processing of a first batch constitutes a first training iteration or training count.

At 608, the system 902 may apply a first masking matrix with a first masking rate to the first sample to mask one or more select elements of the first sample in accordance with the first masking rate. The system 902 may also apply a second masking matrix having a second masking rate to the second sample to mask one or more select elements of the second sample in accordance with the second masking rate. In some embodiments, the first masking rate is the same as the second masking rate. In some embodiments, the first masking rate is different from the second masking rate.

The first and/or second and/or third sampling matrices may be generated by a masking generator 921. The making generator may comprise a pseudo-random number generator. For example, a Python random function may be used. The masking generator 921 may be configured to generate an initialized matrix corresponding to the dimension of a sample to which the masking matrix is to be applied. For example, if the time step of the sample is L, the size of the matrix is L×L. All elements of the initialised matrix comprises the same value, for example, either a '0' or a '1'. The masking generator 921 generates a pseudo random number and determine the masking rate based on the pseudo random number. The masking generator 921 selects one or more elements of the matrix based on the masking rate and masks the selected element(s). For example, the selected elements are updated from a "0" to a "1" or vice versa. Thus, the generated masked matrix may be a two dimensional matrix filled with elements that are either "0" or "1"; "0" may be interpreted as meaning an attention operation in the feature encoder 910 will not be performed, and "1" may be interpreted as meaning an attention operation in the feature encoder 910 will be performed.

At 610, the system 902 provides the masked first sample to a feature encoder 916 to generate a first numerical representation and provides the masked second sample to the feature encoder to generate a second numerical representation.

In some embodiments, the feature encoder 916 is a Transformer based feature encoder. It has been found that Transformer based feature encoder shows promising performance in modelling time-series sequence data due to the self-attention mechanism of Transformer. Since the preprocessed audio data can be seen as time-series data as well, the Transformer may be selected as the feature encoder 910. Table 1 below provides a comparison of the Transformer encoder and other encoders. As discussed below, the Transformer based encoder demonstrated superior performance compared to the others under the same setting (e.g., whether using pre-training or fine-tuning).

In some embodiments, the feature encoder 916 may be a Convolutional Neural Network (CNN) based classifier, such as ResNet and VGG. In some embodiments, the classifier 920 may be a Recurrent Neural Network (RNN) based classifier, or similar, such as Long Short Term Memory (LSTM) networks or Gated Recurrence Units (GRUs). The performance of these two types of feature encoders (VGGish (CNN based feature encoder) and GRU) is presented in Table 1, discussed in detail below.

At 612, the system 902 provides the first and second numerical representations to a machine learning module 918 to generate a first similarity measure indicative of the similarity between the first and second samples. For example, the machine learning module 918 may generate a similarity measure using one of: (i) a cosine similarity metric; and (ii) a bilinear similarity metric.

At 614, the system 902 determines a plurality of second similarity measures. Each second similarity measure may be indicative of the similarity between the first and third samples of each of the negative sample pairs. For example, for each negative sample pair, the system 902 may apply 616 a third masking matrix having a third masking rate to the third sample to mask one or more select elements of the third sample in accordance with the third masking rate, provide 618 the masked third sample to the feature encoder to generate a third numerical representation of the masked third sample, and provide 620 the first numerical representation and the third numerical representation to the machine learning module to generate a second similarity measure between the first and third samples.

At 624, the system 902 determines a loss function value using a loss function based on the first similarity measure, and the plurality of second similarity measures.

At 626, the system 902 adjusts one or more weights of the feature encoder 916 based on the loss function value. The system 902 may also adjust one or more weights of the machine learning module 918 based on the loss function value.

At 628, responsive to the iteration count being less than a threshold value, the system 902 increments the iteration count, and again performs steps 604 to 624. If the iteration count is not less than the threshold value, the process moves to 630.

At 630, responsive to the iteration count reaching or being equal to the threshold value, the system 902 determines the feature encoder as a pre-trained feature encoder.

Figure 7:
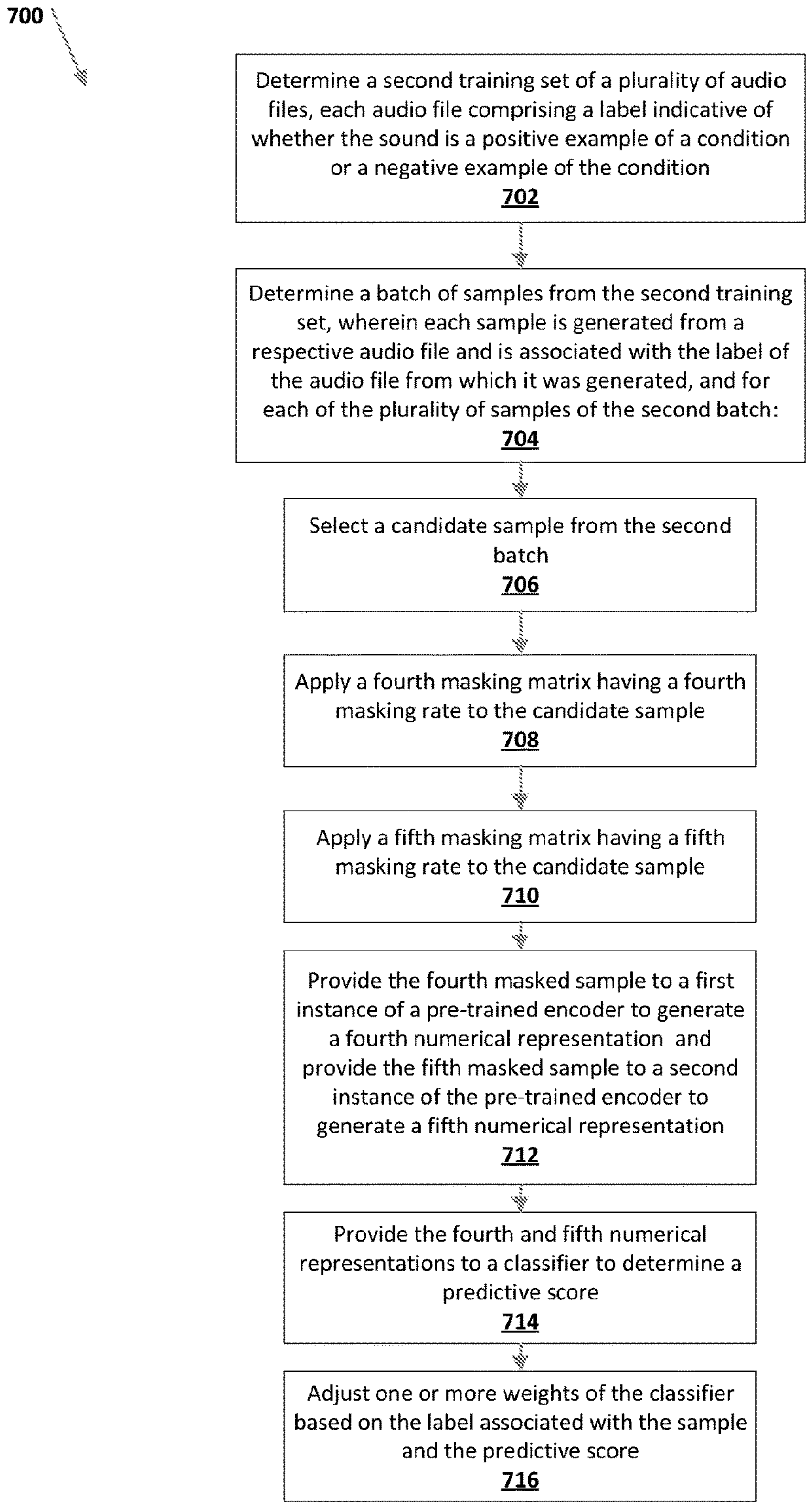
FIG. 7 is a process flow diagram of a method of training a classifier using the pre-trained feature encoder generated according to the method of FIG. 6, according to some embodiments.

FIG. 7 is a process flow diagram of a method 700 for training a classifier, according to some embodiment. The method 700 may, for example, be performed by processor(s) 910 of system 902 executing the modules and/or models stored in memory 912, as discussed in further detail below with reference to FIG. 9. In some embodiments, the method 700 may be performed on a different or disparate system from the system that performed method 600. For example, the system configured to perform method 700 may be configured to receive a pre-trained feature encoder that has been trained elsewhere.

At 702, the system 902 determines a second training set of a plurality of audio files. For example, the system 902 may retrieve the second training set from database 904. Each audio file of the second training set comprises a label indicative of whether the sound of the audio file is a positive example of a condition or a negative example of the condition. For example, the sound may be a respiratory sound, such as a cough, and the condition may be a respiratory condition, such as COVID-19.

At 704, the system 902 determines a batch of samples from the second training set. Each sample may be generated from a respective audio file and may be associated with the label of the audio file from which it was generated. For example, the batch of samples may be generated or sampled from the audio files in a similar manner to the pre-processing of the audio files to generate the samples discussed above in relation to method 600 of FIG. 6, such that they are suitable for providing as inputs to the feature encoder 916.

The system 902 performs 706 to 716 for each of the plurality of samples of the second batch.

At 706, the system 902 selects a candidate sample from the second batch.

The system 902 provides the candidate sample to the pre-trained feature encoder 916 to generate a candidate numerical representation of the candidate sample. In some embodiments, at 708, the system 902 applies a fourth masking matrix having a fourth masking rate to the candidate sample, and at 710, applies a fifth masking matrix having a fifth masking rate to the candidate sample. The fourth and fifth sample rates may be the same or different sampling rates. In some embodiments, at 712, the system 902 provides the fourth masked sample to a first instance of a pre-trained encoder 916 to generate a fourth numerical representation and provides the fifth masked sample to a second instance of the pre-trained encoder 916 to generate a fifth numerical representation.

The system 902 provides the candidate numerical representation(s) or the candidate numerical representation (fourth and fifth masked candidate samples) to a classifier 920 to determine a predictive score. The predictive score may be indicative of the likelihood of the candidate sample being a positive example of the condition.

At 716, the system 902 adjust one or more weights of the classifier 920 based on the label associated with the sample and the predictive score. The system 902 may also adjust one or more weights of the pre-trained feature encode 916 to fine-tune the feature encoder 916.

Once all of the samples of the batch have been applied to the classifier according to the method of FIG. 7, the trained feature encoder 916 and trained classifier 920 (collectively, a trained classification module 928) may be used or deployed elsewhere for use to classify respiratory sounds.

Figure 8:
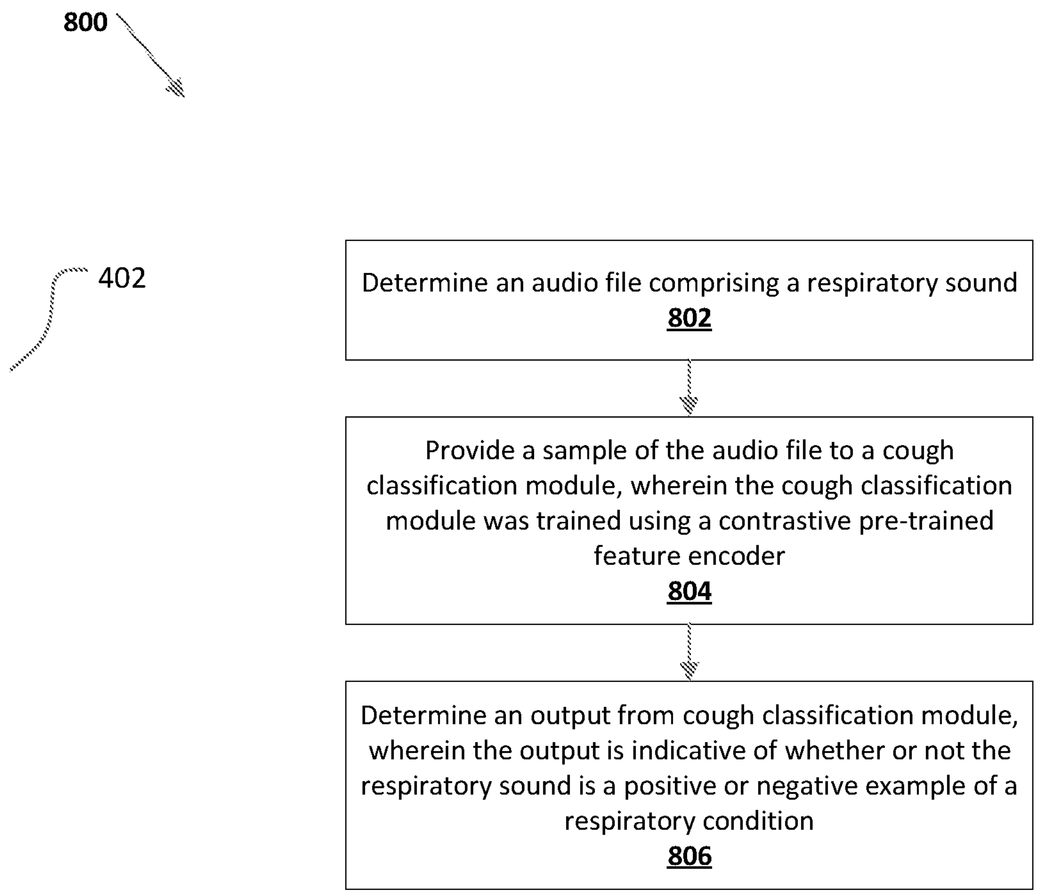
FIG. 8 is a process flow diagram of a method of using the classifier generated according to the method of FIG. 7 to classify a sound sample, according to some embodiments.

FIG. 8 is a process flow diagram of a method 800 for training a feature encoder, according to some embodiment. In some embodiments, the method 800 may be performed by processor(s) 910 of system 902 executing the module(s) and/or model(s) stored in memory 912, as discussed in further detail below with reference to FIG. 9. In some embodiments, the method 800 may be performed by processor(s) 924 of computing device 922 executing the trained classification module 928 stored in memory 926, as discussed in further detail below with reference to FIG. 9.

At 802, the system 902 or computing device 906 determines an audio file comprising a respiratory sound. For example, the audio file may be captured using the computing device 906, such as a microphone (not shown) and audio processing components (not shown) of the computing device 906. Where the system 902 determines the audio file, the audio file may be received by the system from a computing device having the audio file stored thereon, and/or which may have been used to capture the respiratory sound(s) of the audio file. The audio files may be preprocessed in a manner similar to that described above in connection with method 600 of FIG. 6 to generate or sample one or more samples from the audio file.

At 804, the system 902 or computing device 906 provides a sample of the audio file to a trained cough classification module 928. The cough classification module 928 has been trained using a contrastive pre-trained feature encoder 916. The cough classification module 928 comprises a trained feature encoder 916 configured to transform the input sample into a numerical representation of the sample. The numerical representation of the sample is then provided to a cough classifier 920 of the cough classification module 928 to classify the respiratory sound of the sample.

In some embodiments, a masking matrix having an associated masking rate is applied to the sample of the audio file to provide a masked sample, and it is the masked sample that is provided as an input to the trained cough classification module 928.

At 806, the system 902 or computing device 906 determines an output from the cough classifier 920 and cough classification module 928. The output is indicative of whether or not the respiratory sound is a positive or negative example of a respiratory condition.

In some embodiments, the computing device 906 may be provided to a user of the computing device 906 via the user interface 930, for example, as a display or an audio output.

In some embodiments, the output may be transmitted, by the system 902 or computing device 96, to a user device, such as a computing device 906, associated with the individual identified as being associated with the audio sample, or, for example, a clinician. For example, the output may be emailed or provided as an SMS to the computing device 906.

Figure 9:
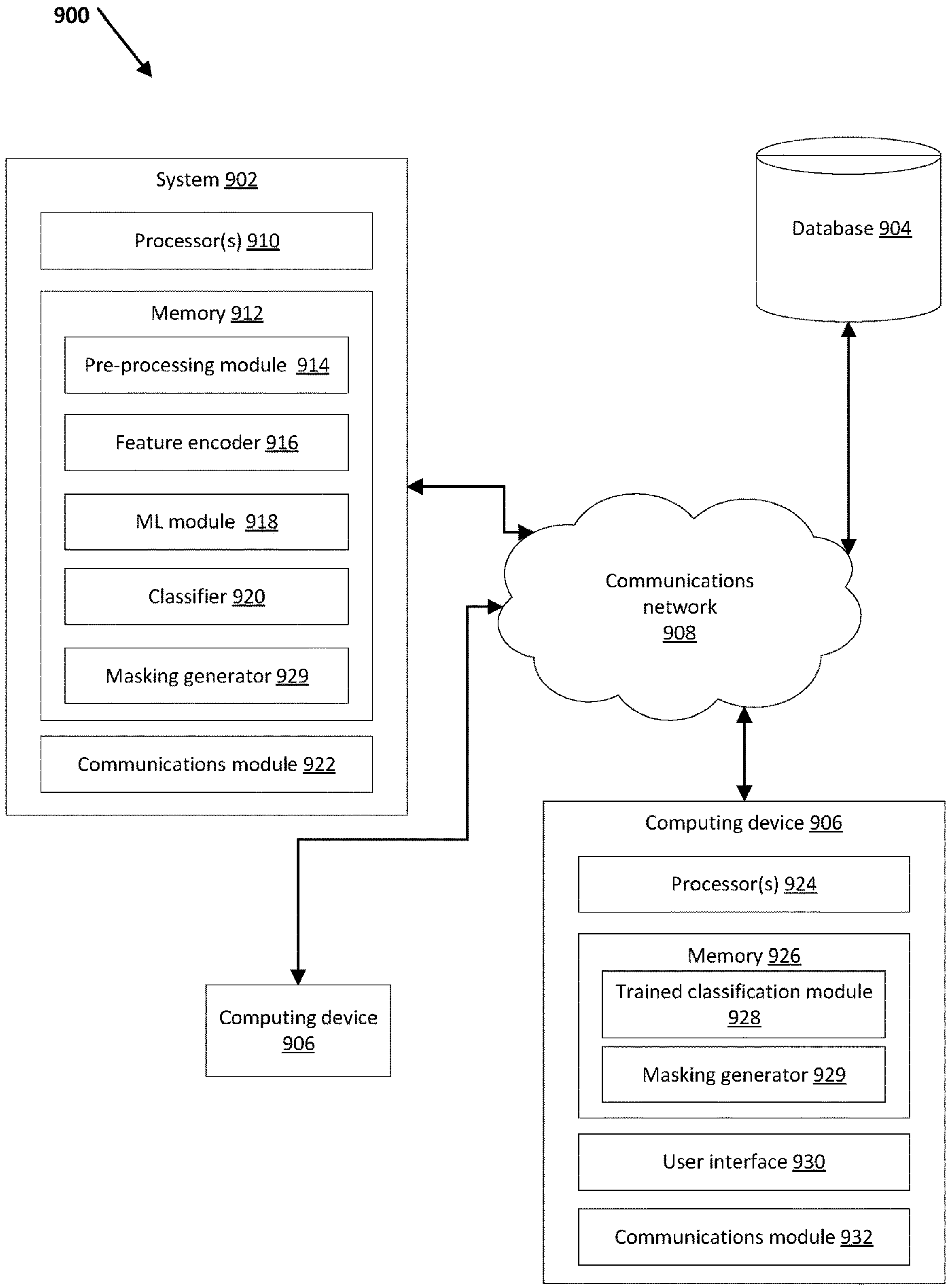
FIG. 9 is a schematic of a communications network comprising a system in communication with a database and one or more computing devices across a communications network.

Referring now to FIG. 9, there is illustrated a schematic of a communications network 900 comprising a system 902. The system 902 may be in communication with database(s) 904 and/or and one or more computing devices 906 across a communications network 908. Examples of a suitable communications network 908 include a cloud server network, wired or wireless internet connection, Bluetooth™ or other near field radio communication, and/or physical media such as USB.

The system 902 may comprise one or more servers configured to perform functionality and/or provide services to user devices, such as the one or more computing devices 906. The system 902 comprises one or more processors 910 and memory 912 storing instructions (e.g. program code) which when executed by the processor(s) 910 causes the system 902 to function according to the described methods. The processor(s) 910 may comprise one or more microprocessors, central processing units (CPUs), graphical/graphics processing units (GPUs), application specific instruction set processors (ASIPs), application specific integrated circuits (ASICs) or other processors capable of reading and executing instruction code.

Memory 912 may comprise one or more volatile or non-volatile memory types. For example, memory 912 may comprise one or more of random access memory (RAM), read-only memory (ROM), electrically erasable programmable read-only memory (EEPROM) or flash memory. Memory 912 is configured to store program code accessible by the processor(s) 910. The program code comprises executable program code modules. In other words, memory 912 is configured to store executable code modules configured to be executable by the processor(s) 910. The executable code modules, when executed by the processor(s) 910 cause the system 902 to perform certain functionality, as described in more detail below.

Memory 912 may comprise a pre-processing module 914 configured to pre-process and prepare audio files and/or samples for processing by the feature encoder 916, as discussed above with reference to method 600 of FIG. 6. Memory 912 comprises the feature encoder 916, which is configured to encode or transform feature matrices of samples of audio sounds into numerical representations for processing by or providing as inputs to a machine learning (ML) module 918 or a classifier 920. Memory 912 comprises the ML module 918, which is configured to receive as inputs, numerical representation of two samples and generate a similarity measure indicative of the similarity between the two samples. Memory 912 comprises a classifier 920 configured to receive as an input, a numerical representation of a sample from the feature encoder 916, and provide as an output a predictive score indicative of the likelihood of the sample being a positive example of a particular condition, such as a respiratory condition. Memory 912 may comprise a masking generator 929 for generating masking matrices with respective masking rates to be applied to samples. The masking generator 929 may generate a masking rate randomly. In some embodiments, the masking generator 929 may generate a masking rate of less than 75%. In some embodiments, the masking generator 929 may generate a masking rate of between 25% and 75%. In some embodiments, the masking generator 929 may generate a masking rate of between 40% and 60%. In some embodiments, the masking generator 929 may generate a masking rate of 50%.

The system 902 further comprises a network interface 922 to facilitate communications with components of the architecture 900 across the communications network 908, such as the one or more computing devices 906, database 904 and/or other systems or servers (not shown). The network interface 922 may comprise a combination of network interface hardware and network interface software suitable for establishing, maintaining and facilitating communication over a relevant communication channel.

The database 904 may form part of, or be local to, the system 902, or may be remote from and accessible to the system 902. The database 904 may be configured to store a plurality of audio files associated with a respective plurality of individuals. Each audio file may be associated with one or more identifiers. In some embodiments, the one or more audio files may be associated with a unique identifier configured to identify one audio file from another. In some embodiments, one or more audio files may be associated with an identifier indicative of the individual associated with the sound of the audio file, i.e., the individual that made the sound, such as a respiratory sound of the individual. In some embodiments, at least some of the audio files are associated with a label indicative of whether the sound of the audio file is a positive or a negative example of a respiratory condition, such as COVID-19 (labeled audio files). The database 904 may be configured to store user details or encrypted credentials, such as username(s), password(s), biometric data and/or other user data associated with the audio files. The system 902, and in some embodiments, the computing device(s) 906, may be configured to retrieve audio files from the database 904 for processing.

The computing device(s) 906 may be a mobile device, a tablet, a laptop computer, a smart sensor or any other suitable device. The computing device(s) 906 may comprise one or more processors 924 and memory 926 storing instructions (e.g. program code), which when executed by the processor(s) 924, causes the computing device(s) 906 to perform certain functionality, including, for example, the method of FIG. 8. To this end, memory 926 may comprise a trained classification module 928. The trained classification module 928 may comprise a feature encoder 916 and a trained classifier 920, which have been trained according to methods 600 and 700 of FIGS. 6 and 7, respectively. Memory 926 may comprise the masking generator 929 for generating masking matrices with respective masking rates to be applied to samples.

The computer device(s) 906 may comprise a user interface 930 to provide outputs to users, such as individuals, patients, and/or clinicians. For example, the user interface 930 may comprise one or more displays, touchscreens, light indicators (LEDs), sound generators and/or haptic generators which may be configured to provide feedback (e.g. visual, auditory or haptic feedback) to a user.

The computing device(s) 906 may comprise a network interface or communications module 932 to facilitate communication with the components of the communications network 110, such as the system 902 and/or database 904 and/or other computing devices.

Evaluation

Experimental Setup

For the evaluation of the described embodiments, two public COVID-19 respiratory datasets were used; the Coswara dataset and the COVID-19 Sounds dataset.

The Coswara dataset (N Sharma, P Krishnan, R Kumar, S Ramoji, SR Chetupalli, R Nirmala, P Kumar Ghosh, and S Ganapathy. 2020. Coswara-A database of breathing, cough, and voice sounds for COVID-19 diagnosis. In Proceedings of the Annual Conference of the International Speech Communication Association, INTERSPEECH, Vol. 2020. International Speech Communication Association, 4811-4815) is part of Project Coswara5 which aims to build a diagnostic tool for COVID-19 based on respiratory, cough, and speech sounds. Upon until Dec. 21, 2020, there are 1,486 crowd-sourced samples (collected from 1,123 males and 323 females) available at Coswara data repository6. The majority of the participants are from India (1,329 participants) and the rest participants are from other countries of five continents: Asia, Australia, Europe, North America, and South America. Four types of sounds (breathing, coughing, counting, and sustained phonation of vowel sounds) are gathered from each participant.

Similar to Coswara dataset, COVID-19 Sounds is another crowdsourcing based respiratory sound dataset. Audios are collected world-widely with a web-based app, an Android app, and an Apple app. The same curated dataset that is introduced and used in Brown et al (Chloe Brown, Jagmohan Chauhan, Andreas Grammenos, Jing Han, Apinan Hasthanasombat, Dimitris Spathis, Tong Xia, Pietro Cicuta, and Cecilia Mascolo. 2020. Exploring Automatic Diagnosis of COVID-19 from Crowdsourced Respiratory Sound Data. In KDD '20: The 26th ACM SIGKDD Conference on Knowledge Discovery and Data Mining, Virtual Event, CA, USA, Aug. 23-27, 2020, Rajesh Gupta, Yan Liu, Jiliang Tang, and B. Aditya Prakash (Eds.). ACM, 3474-3484. https://dl.acm.org/doi/10.1145/3394486.3412865) was used. After filtering out silent and noisy samples, in this released version of dataset7, there are 141 COVID-19 positive audio recordings collected from 62 participants and 298 COVID-19 negative audio recordings from 220 participants. Both coughs and breaths appear in these recordings. Positive samples are from participants who claimed that they had tested positive for COVID-19.

Because the Coswara dataset has more participants and contains more audio samples than COVID-19 Sounds dataset, the Coswara dataset was adopted as the pre-training dataset for phase one. Note that for this pre-training dataset, the annotated labels (indicating whether the user is COVID-19 positive or negative) are not used. Furthermore, respiratory sounds including breathing sounds and cough sounds were specifically selected for pre-processing and sampling, whereas audios of sustained phonation of vowel sounds and counting sounds were ignored in the pre-training phase. Consequently, COVID-19 Sounds is used as the dataset in the second (downstream) phase. To be more specific, in the downstream phase, the whole COVID-19 Sounds dataset is randomly divided into the training set (70%), validation set (10%), and testing set (20%). For each raw audio sample for the second phase, the same pre-processing procedure is applied as well, as described above in relation to method 600 of FIG. 6.

Implementation Details

In the pre-processing, the shape of a processed clip $a_i$ is $R^{64\times 96}$ as the number of mel-spaced frequency bins N is set to 64 and the sliding window size $T_w$ is 96, which corresponds to 960 ms. The feature dimension d is set to 64. In the contrastive pre-training phase, the batch size B is selected as a relatively large number (1024). The contrastive learning may benefit from larger batch sizes (within GPU capacity) because a larger batch allows the machine learning model or module to compare the positive pair against more negative pairs. In the downstream network, the dropout is also applied to avoid over-fitting in the end-to-end fine-tuning process. The validation set in the downstream dataset is used for tuning hyperparameter d (the feature dimension of the feature encoder) and the dropout rate. The batch size is 128 for the downstream phase. All experiments (both the contrastive pre-training and the downstream phases) are trained with Adam optimiser (Diederik P. Kingma and Jimmy Ba. 2015. Adam: A Method for Stochastic Optimization. In 3rd International Conference on Learning Representations, ICLR 2015, San Diego, CA, USA, May 7-9, 2015, Conference Track Proceedings, Yoshua Bengio and Yann LeCun (Eds.).), a 0.001 initial learning rate with ReduceLROnPlateau9 decay setting, and executed on a desktop with an NVIDIA GeForce RTX-2080 Ti GPU with PyTorch.

Evaluation Metrics

To evaluate the performance of different methods, several standard classification evaluation metrics including the Receiver Operating Characteristic-Area Under Curve (ROC-AUC), Precision, and Recall were selected. The experiments demonstrate the average performance as well as the standard deviation of five runnings of each method or configuration, and the average F1 score which is calculated based on the average Precision and average Recall.

Hyperparameter Fine-Tuning

Figure 5:
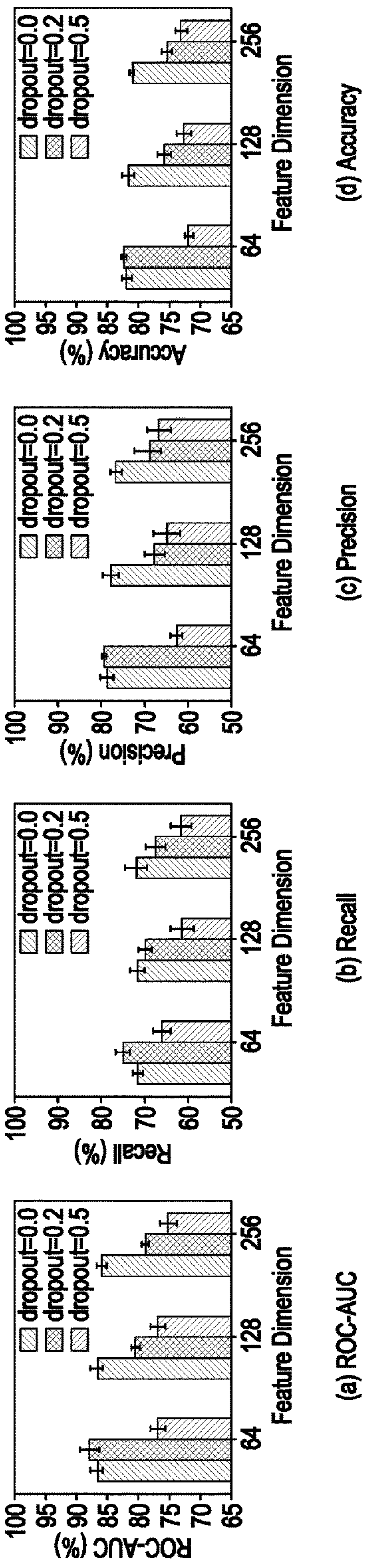
FIGS. 5(*a*) to 5(*d*) are graphical representations comparing Receiver Operating Characteristic-Area Under Curve (ROC-AUC), recall, precision and accuracy, respectively, of different feature dimensions and drop-out rates.

To investigate how the dimension of encoded feature and dropout rate influence the classification performance, all the combination of the following hyperparameter values (within reasonable ranges) were evaluated on the validation set: (1) Feature Dimension: [64, 128, 256]; (2) Dropout Rate: [0.0, 0.2, 0.5] (resulting in 9 combinations in total); each combination was run five times. FIG. 5 shows the average performance of the four metrics and error bars indicate the standard deviations. Based on these validation results, d=64 and a 0.2 dropout rate were found to achieve the best validation performance and were used for the remaining experiments. Since the feature encoder structure should be identical in both the pre-training and the downstream phases, the same hyperparameter setting is also applied in the pre-training phase.

Contrastive Pre-Training Performance

Methods for Comparison

To evaluate the performance of contrastive pre-training and the Transformer feature encoder, the Transformer feature encoder, Transformer-CP (the suffix -CP meaning the feature encoder is contrastive pre-training enabled), is compared with several techniques with multiple configurations. Other techniques being compared include VG-Gish/GRU/Transformer (without contrastive pre-training) and GRU-CP. Recurrent Neural Networks (RNNs) are designed for handling sequence data and so, the GRU (Junyoung Chung, Caglar Gulcehre, KyungHyun Cho, and Yoshua Bengio. 2014. Empirical Evaluation of Gated Recurrent Neural Networks on Sequence Modeling. arXiv preprint arXiv: 1412.3555 (2014).) is also included in the comparison. VGGish (Shawn Hershey, Sourish Chaudhuri, Daniel P W Ellis, Jort F Gemmeke, Aren Jansen, R Channing Moore, Manoj Plakal, Devin Platt, Rif A Saurous, Bryan Seybold, et al. 2017. CNN architectures for large-scale audio classification. In 2017 ieee international conference on acoustics, speech and signal processing (icassp). IEEE, 131-135.) is a popular convolutional neural network for audio classification. A pre-trained version10 that is pre-trained on a large scale general audio dataset Audioset (Jort F Gemmeke, Daniel P W Ellis, Dylan Freedman, Aren Jansen, Wade Lawrence, R Channing Moore, Manoj Plakal, and Marvin Ritter. 2017. Audio set: An ontology and human-labeled dataset for audio events. In 2017 IEEE International Conference on Acoustics, Speech and Signal Processing (ICASSP). IEEE, 776-780.) is also used in the community.

The configuration of with or without the pre-training is summarised in the third column of Table 1, below. In addition, the second column indicates the pre-training setting. A ✓ means that the proposed self-supervised contrastive pre-training is applied. For example, both the second and third columns are ✓ for our Transformer-CP.

TABLE 1

Results (on the testing set) of different models and configurations. For each result, the standard deviation is reported in a bracket.

| Model | Self-supervise | Pre-train | Fine-tune | ROC-AUC | Recall | Precision | Accuracy | Average F1 |
|---|---|---|---|---|---|---|---|---|
| VGGish | X | X | N/A | 76.14 (0.21) | 53.19 (2.29) | 73.17 (1.87) | 74.88 (0.22) | 61.60 |
| | X | ✓ | X | 85.02 (1.73) | 67.42 (2.06) | 78.55 (2.21) | 80.71 (1.32) | 72.56 |
| | X | ✓ | ✓ | 87.34 (1.14) | 69.49 (1.44) | 83.15 (1.46) | 83.12 (0.31) | 75.71 |
| GRU | X | X | N/A | 84.43 (0.88) | 65.60 (1.43) | 82.67 (1.89) | 81.76 (0.39) | 73.15 |
| Transformer | X | X | N/A | 87.60 (0.71) | 71.53 (1.12) | 80.64 (1.19) | 82.73 (0.41) | 75.81 |
| GRU-CP | ✓ | ✓ | X | 83.20 (0.43) | 63.43 (1.82) | 78.63 (1.22) | 79.63 (0.31) | 70.22 |
| | ✓ | ✓ | ✓ | 87.08 (0.35) | 71.72 (2.53) | 81.61 (2.26) | 83.15 (0.32) | 76.35 |
| Transformer- | ✓ | ✓ | X | 84.34 (0.71) | 64.94 (1.80) | 78.56 (1.40) | 80.02 (0.42) | 71.10 |
| CP | ✓ | ✓ | ✓ | 88.83 (0.53) | 73.07 (0.65) | 81.99 (0.92) | 83.74 (0.39) | 77.27 |

Performance Comparison

The experimental results of the above techniques are reported in Table 1. To be more specific, for techniques using pre-trained weights (either contrastive pre-training or conventional pre-training for VGGish), the fine-tuning option was also explored. In the fourth column of Table 1, an "x" represents that the pre-trained weights Wf are frozen and not be updated in the downstream phase, whereas a "✓" indicates that the Wf is allowed to be updated.

According to the results of Table 1, the Transformer-CP of the described embodiments, with fine-tuning, achieves the best performance (shown in bold) against all the other techniques. There are several additional findings that can be noticed from the table. First, without pre-training, VGGish has the worst performance (the first row) compared to GRU and Transformer. Using pre-trained VGGish weights (without fine-tuning) provides almost 6% accuracy gain, which indicates that the pre-trained VGGish representation is well-trained and powerful. Of all configurations that use frozen pre-trained representations (the second, sixth, and eighth rows), although VGGish (the second row) is the top performer, the performance of our Transformer-CP (the eighth row) is very close to VGGish. It may therefore be understood that the contrastive pre-trained (on a smaller scale and unlabelled dataset) self-supervised feature representation of the described embodiments is competitive with a well-trained fully-supervised VGGish representation (pre-trained on a much larger scale and well-annotated Audioset). Second, the fine-tuning in the downstream task is important for all pre-trained models, which is as expected. For both the conventional pre-trained VGGish and contrastive pre-trained GRU/Transformer, the fine-tuning could improve the accuracy by around 3%. Third, when comparing GRU vs.

Transformer and GRU-CP vs. Transformer-CP, the Transformer-based techniques outperform GRU-based techniques consistently. Overall, the results show that the framework with contrastive pre-training of the described embodiments achieves a superior performance of cough classification.

Different Similarity Metrics

In Table 2 below, two similarity metrics in contrastive learning were compared. For a fair comparison, two different feature encoder structures, GRU-CP and Transformer-CP, were also explored. As shown in the table, using bilinear similarity achieves consistent better performance with both structures on all evaluation metrics, which demonstrates that the bilinear similarity is more suitable for a cough classification task.

TABLE 2

Results (on the testing set) of two types of similarity metrics that are used in the contrastive pre-training phase.

| Model | Similarity Metric | ROC-AUC | Recall | Precision | Accuracy | Average F1 |
|---|---|---|---|---|---|---|
| GRU-CP | Cosine | 87.08 (0.35) | 71.72 (2.53) | 81.61 (2.26) | 83.15 (0.32) | 76.35 |
| | Bilinear | 87.25 (0.65) | 71.99 (1.97) | 82.62 (1.92) | 83.65 (0.32) | 76.94 |
| Transformer-CP | Cosine | 87.02 (0.53) | 67.79 (2.12) | 81.73 (1.54) | 82.06 (0.33) | 74.11 |
| | Bilinear | 88.83 (0.53) | 73.07 (0.65) | 81.99 (0.92) | 83.74 (0.39) | 77.27 |

Random Masking Performance

The random masking mechanism and different masking rates in the contrastive pre-training phase of the described embodiments was also tested. The experiment guideline for these tests involved pre-training several Transformer-CPs with multiple masking rates (0% to 100%) and then fine-tuning the pre-trained models in the downstream phase. The cough classification performance of these classification models are listed in Table 3. Please note that in the downstream phase, we the ensemble architecture was not applied, and so there is no random masking in the downstream phase for results reported in the table.

TABLE 3

Cough classification results (on the testing set) of different masking rates used in the contrastive pre-training phase.

| Model | Masking Rate (CP) | ROC-AUC | Recall | Precision | Accuracy | Average F1 |
|---|---|---|---|---|---|---|
| Transformer | NA | 87.60 (0.71) | 71.53 (1.12) | 80.64 (1.19) | 82.73 (0.41) | 75.81 |
| Transformer-CP | 0% | 88.83 (0.53) | 73.07 (0.65) | 81.99 (0.92) | 83.74 (0.39) | 77.27 |
| | 25% | 89.17 (0.13) | 73.05 (0.83) | 82.29 (1.13) | 83.84 (0.38) | 77.40 |
| | 50% | 89.42 (0.51) | 73.09 (0.43) | 83.26 (0.28) | 84.26 (0.12) | 77.84 |
| | 75% | 89.13 (0.95) | 72.66 (1.20) | 82.01 (1.52) | 83.62 (0.41) | 77.05 |
| | 100% | 88.37 (0.57) | 72.41 (0.64) | 81.65 (0.82) | 83.41 (0.41) | 76.75 |

As a baseline for comparison, the performance of Transformer (without any pre-training) in Table 3 is also included. In general, all pre-trained models yield better results than the baseline Transformer and 50% masking outperforms other masking rates. When the masking rate is increasing from 0% (no masking at all) to 50%, a performance gain is observed from the table. However, when the masking rate is too large (e.g., 75% and 100%), the performance decreases. This is not surprising. For example, in the extreme 100% masking case, all the inputs would be masked, which would mean that there is no attention between any time steps. As a result, the 100% masking has the worst performance among different masking rate settings.

Ensembles Performance

Different ensembles performance was also explored. Table 4 below summarises three ensemble methods. The first two are the ensemble of the Transformer feature encoder and other feature encoder structures (VGGish and GRU). No pre-trained weights were applied to these two ensembles. The third ensemble combines GRU-CP and Transformer-CP with contrastive pre-trained weights. By jointly comparing results given in Table 1 and Table 4, it can be seen that the ensemble version demonstrates a better ability than a single feature encoder based method.

TABLE 4

Cough classification results (on the testing set) of different ensemble configurations.

| Ensemble_1 | Ensemble_2 | ROC-AUC | Recall | Precision | Accuracy | Average F1 |
|---|---|---|---|---|---|---|
| VGGish | Transformer | 87.58 (0.73) | 70.30 (1.05) | 82.46 (1.44) | 83.10 (0.26) | 75.90 |
| GRU | Transformer | 87.24 (0.59) | 72.56 (1.81) | 81.10 (1.54) | 83.20 (0.38) | 76.59 |
| GRU-CP | Transformer-CP | 88.90 (0.38) | 72.77 (1.85) | 83.59 (1.62) | 84.04 (0.35) | 77.81 |

TABLE 5

Results (on the testing set) of combining different masking rates with ensembles in the downstream phase.

| Ensemble_1 | Ensemble_2 | Masking (DS) | ROC-AUC | Recall | Precision | Accuracy | Average F1 |
|---|---|---|---|---|---|---|---|
| Transformer-CP | Transformer-CP | 0% | 88.77 (0.87) | 71.98 (0.67) | 82.81 (0.59) | 83.75 (0.38) | 77.02 |
| | | 25% | 89.02 (0.55) | 71.93 (1.01) | 82.85 (0.48) | 84.15 (0.20) | 77.00 |
| | | 50% | 90.03 (0.41) | 73.24 (0.22) | 84.57 (1.24) | 84.43 (0.25) | 78.50 |
| | | 75% | 89.22 (0.24) | 72.12 (0.32) | 83.17 (0.21) | 84.03 (0.58) | 77.25 |
| | | 100% | 89.55 (0.91) | 71.21 (1.79) | 82.85 (2.33) | 83.93 (0.17) | 76.59 |

Networks where the random masking is incorporated with the ensemble architecture were also investigated (as shown in FIG. 4). For the ensembles presented in Table 5 above, both branches are set as Transformer-CP. The masking rate in the downstream phase was manipulated (rates given in the Masking (DS) column). In addition, the pre-trained weights of the top performer in Table 3 (with 50% contrastive pre-training masking rate) were used for these ensembles. Similar to the masking in the contrastive pre-training phase, 50% masking rate in the downstream phase also performs better than other masking rates. The above results confirm that the proposed ensemble architecture with the random masking could further improve the classification performance.

Inference Speed

TABLE 6

Comparison of inference speed of different model and configurations. Each method is benchmarked on the same NVIDIA Geforce RTX-2080 Ti GPU.

| Ensemble | Model | Self-supervise | Pre-train | Masking Rate (DS) | Inference time ($10^{-6}$ seconds) |
|---|---|---|---|---|---|
| X | VGGish | X | X | N/A | 6.39 |
| | | X | ✓ | N/A | 6.39 |
| | GRU | X | X | N/A | 8.34 |
| | Transformer | X | X | N/A | 8.48 |
| | GRU-CP | ✓ | ✓ | N/A | 8.60 |
| | Transformer-CP | ✓ | ✓ | N/A | 8.52 |
| ✓ | VGGish + Transformer | X | X | N/A | 12.58 |
| | GRU + Transformer | X | X | N/A | 14.26 |

TABLE 6-continued

Comparison of inference speed of different model and configurations.
Each method is benchmarked on the same NVIDIA Geforce RTX-2080 Ti GPU.

| Ensemble | Model | Self-supervise | Pre-train | Masking Rate (DS) | Inference time ($10^{-6}$ seconds) |
|---|---|---|---|---|---|
| | GRU-CP + Transformer-CP | ✓ | ✓ | N/A | 14.36 |
| | Transformer-CP + | ✓ | ✓ | 0% | 18.86 |
| | Transformer-CP | ✓ | ✓ | 25% | 24.53 |
| | | ✓ | ✓ | 50% | 27.56 |
| | | ✓ | ✓ | 75% | 32.36 |
| | | ✓ | ✓ | 100% | 18.64 |

Table 6 lists the inference time (for one input instance) of each model or configuration. Since the fine-tuning does not affect the inference time, the fine-tuning configuration is removed for comparison in the table. Generally, for three different base feature encoder structures, the inference time of Transformer is on par with GRU, whereas VGGish leads Transformer/GRU by a small margin (around 0.002 milliseconds only). Although Transformer includes attention computation, it processes each time step in the input sequence in parallel, whereas GRU has to process each time step re-currently. This might explain the similar computation cost between Transformer and GRU. From the table, it appears that using contrastive pre-trained weights does not introduce a longer time for inference. This is as expected as the major difference between Transformer and Transformer-CP (or GRU vs. GRU-CP) is whether loading the pre-trained weights. This weights initialisation process appears to have almost has no influence on the inference speed.

An interesting and surprising finding is about the inference time of using different downstream random masking rates (the last five rows of Table 6). In theory, a larger masking rate would be expected to run faster as more time steps are masked and not used in attention calculation. According to the table, however, 75% rate has the largest inference time and 0% and 100% are all smaller than the rest masking rates. This can be explained by the implementation of the masking generator. In the implementation, the default masking matrix is an all-ones matrix or an all-zeros matrix (only used for masking rate 100%), where 0 means being masked and vice versa. For a given masking rate, 1 will be updated to 0 in the matrix through a "for" loop. This loop operation takes longer if more elements need to be updated (e.g., 75% rate), which causes the larger inference time for the 75% setting. Overall, even the largest time cost in the table is only 32.36x10–6 seconds (around 0.03 milliseconds). Such a low time cost is unlikely to be a bottleneck or limit the application of the proposed framework.

From another point of view, without the contrastive pre-training methodology of the described embodiments, multiple models need to be trained if multiple datasets are available. As a result, training time will likely be done per model without domain transfer, which is a potential bottleneck for large-scale deployments. However, the described embodiments addresses this training bottleneck through the contrastive pre-training phase.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A system comprising:

one or more processors; and memory comprising computer executable instructions, which when executed by the one or more processors, cause the system to:

a) determine a first training set comprising a plurality of audio files, wherein each audio file comprises a respiratory sound;

b) determine a database comprising a plurality of samples for each of the audio files of the first training set, wherein each sample is associated with an identifier, wherein determining the database comprising the plurality of samples comprises:

i) transforming each audio file into a feature matrix, each feature matrix comprising a first dimension corresponding to a number of frequency bins, and a second dimension corresponding to a number of time frames in the audio file;

ii) for each feature matrix, generating at least one sample, each sample comprising the first dimension corresponding to a number of frequency bins, and a third dimension corresponding to a predefined number of time frames, wherein the third dimension is a subset of the second dimension;

c) determine a batch of sample pairs from the database, wherein the batch comprises one positive sample pair comprising a first sample and second sample, wherein the first sample and the second sample are associated with a common identifier, and the batch comprises a plurality of negative sample pairs, each negative sample pair comprising the first sample and a respective third sample, wherein the identifier associated with each respective third sample is different to the identifier associated with the first sample;

d) apply a first masking matrix having a first masking rate to the first sample to mask one or more select elements of the first sample in accordance with the first masking rate;

e) provide the masked first sample to a feature encoder to generate a first numerical representation of the masked first sample;

f) apply a second masking matrix having a second masking rate to the second sample to mask one or more select elements of the second sample in accordance with the second masking rate;

g) provide the masked second sample of the positive candidate pair to the feature encoder to generate a second numerical representation of the masked second sample;

h) provide the first numerical representation and the second numerical representation to a neural network to generate a first similarity measure indicative of the similarity between the masked first and second samples of the positive candidate pair;

i) determine a plurality of second similarity measures, each second similarity measure being indicative of the similarity between the first and third samples of each of the negative sample pairs, wherein said determining comprises:

for each negative sample pair:

i) apply a third masking matrix having a third masking rate to the third sample to mask one or more select elements of the third sample in accordance with the third masking rate;

ii) provide the masked third sample to the feature encoder to generate a third numerical representation of the masked third sample; and iii) provide the first numerical representation and the third numerical representation to the neural network to generate a second similarity measure between the first and third samples;

j) determine a loss function value using a loss function based on the first similarity measure, and the plurality of second similarity measures;

k) adjust one or more of weights of the feature encoder based on the determined loss function value;

l) Responsive to a iteration count being less than a threshold value:

i) increment the iteration count; and ii) repeat c) to k);

m) responsive to the iteration count reaching the threshold value, determine the feature encoder as a pre-trained feature encoder.

2. The system of claim 1, wherein the computer executable instructions, which when executed by the one or more processors, further cause the system to:

a) determine a second training set of a plurality of audio files, each audio file comprising a label indicative of whether the sound is a positive example of a condition or a negative example of the condition;

b) generate a batch of samples from the second training set, wherein each sample is generated from a respective audio file and is associated with the label of the audio file from which it was generated; and c) for each of the plurality of samples of the second batch:

i) select a candidate sample from the second batch;

ii) provide the candidate sample to the pre-trained feature encoder to generate a candidate numerical representation of the candidate sample;

iii) provide the candidate numerical representation to a classifier to determine a predictive score, wherein the predictive score is indicative of the candidate sample being a positive example of the condition; and iv) adjust one or more weights of the classifier based on the label associated with the candidate sample and the predictive score.

3. The system of claim 2, wherein the pre-trained feature encoder comprises a first pre-trained feature encoder and a second pre-trained feature encoder, and wherein the computer executable instructions, which when executed by the one or more processors, cause the system to provide the candidate sample to the pre-trained feature encoder further cause the system to:

a) apply a fourth masking matrix having a fourth masking rate to the candidate sample to mask one or more select elements of the candidate sample in accordance with the fourth masking rate to provide a fourth masked sample;

b) apply a fifth masking matrix having a fifth masking rate to the candidate sample to mask one or more select elements of the candidate sample in accordance with the fifth masking rate to provide a fifth masked sample; and c) provide the fourth masked sample to the first pre-trained encoder to generate a fourth numerical representation of the fourth masked sample and providing the fifth masked sample to the second pre-trained encoder to generate a fifth numerical representation of the fifth masked sample; and wherein providing the candidate numerical representation to the classifier comprises providing both the fourth numerical representation and the fifth numerical representation as inputs to the classifier.

4. The system of claim 1, wherein the audio files of the first training set do not include labels indicative of whether the sound of the audio file is a positive example of a condition or a negative example of the condition.

5. The system of claim 1, wherein each of the plurality of samples comprises at least a portion of a sound of a respective audio file.

6. A method comprising:

a) determining a first training set comprising a plurality of audio files, wherein each audio file comprises a respiratory sound;

b) determining a database comprising a plurality of samples for each of the audio files of the first training set, wherein each sample is associated with an identifier, wherein determining the database comprising the plurality of samples comprises:

i) transforming each audio file into a feature matrix, each feature matrix comprising a first dimension corresponding to a number of frequency bins, and a second dimension corresponding to a number of time frames in the audio file;

ii) for each feature matrix, generating at least one sample, each sample comprising the first dimension corresponding to a number of frequency bins, and a third dimension corresponding to a predefined number of time frames, wherein the third dimension is a subset of the second dimension;

c) determining a batch of sample pairs from the database, wherein the batch comprises one positive sample pair comprising a first sample and second sample, wherein the first sample and the second sample are associated with a common identifier, and the batch comprises a plurality of negative sample pairs, each negative sample pair comprising the first sample and a respective third sample, wherein the identifier associated with each respective third sample is different to the identifier associated with the first sample;

d) applying a first masking matrix having a first masking rate to the first sample to mask one or more select elements of the first sample in accordance with the first masking rate;

e) providing the masked first sample to a feature encoder to generate a first numerical representation of the masked first sample;

f) applying a second masking matrix having a second masking rate to the second sample to mask one or more select elements of the second sample in accordance with the second masking rate;

g) providing the masked second sample of the positive candidate pair to the feature encoder to generate a second numerical representation of the masked second sample;

h) providing the first numerical representation and the second numerical representation to a neural network to generate a first similarity measure indicative of the similarity between the masked first and second samples of the positive candidate pair;

i) determining a plurality of second similarity measures, each second similarity measure being indicative of the similarity between the first and third samples of each of the negative sample pairs, wherein said determining comprises:

for each negative sample pair:

i) applying a third masking matrix having a third masking rate to the third sample to mask one or more select elements of the third sample in accordance with the third masking rate;

ii) providing the masked third sample to the feature encoder to generate a third numerical representation of the masked third sample; and iii) providing the first numerical representation and the third numerical representation to the neural network to generate a second similarity measure between the first and third samples;

j) determining a loss function value using a loss function based on the first similarity measure, and the plurality of second similarity measures;

k) adjusting one or more of weights of the feature encoder based on the determined loss function value;

l) Responsive to an iteration count being less than a threshold value:

i) incrementing the iteration count; and ii) repeating steps c) to k);

m) responsive to the iteration count reaching the threshold value, determining the feature encoder as a pre-trained feature encoder.

7. The method of claim 6, further comprising:

a) determining a second training set of a plurality of audio files, each audio file comprising a label indicative of whether the sound is a positive example of a condition or a negative example of the condition;

b) generating a batch of samples from the second training set, wherein each sample is generated from a respective audio file and is associated with the label of the audio file from which it was generated; and c) for each of the plurality of samples of the second batch:

i) selecting a candidate sample from the second batch;

ii) providing the candidate sample to the pre-trained feature encoder to generate a candidate numerical representation of the candidate sample;

iii) providing the candidate numerical representation to a classifier to determine a predictive score, wherein the predictive score is indicative of the candidate sample being a positive example of the condition; and iv) adjusting one or more weights of the classifier based on the label associated with the candidate sample and the predictive score to generate a trained classifier.

8. The method of claim 7, wherein the pre-trained feature encoder comprises a first pre-trained feature encoder and a second pre-trained feature encoder, and wherein providing the candidate sample to the pre-trained feature encoder comprises:

a) applying a fourth masking matrix having a fourth masking rate to the candidate sample to mask one or more select elements of the candidate sample in accordance with the fourth masking rate to provide a fourth masked sample;

b) applying a fifth masking matrix having a fifth masking rate to the candidate sample to mask one or more select elements of the candidate sample in accordance with the fifth masking rate to provide a fifth masked sample; and c) providing the fourth masked sample to the first pre-trained encoder to generate a fourth numerical representation of the fourth masked sample and providing the fifth masked sample to the second pre-trained encoder to generate a fifth numerical representation of the fifth masked sample; and wherein providing the candidate numerical representation to the classifier comprises providing both the fourth numerical representation and the fifth numerical representation as inputs to the classifier.

9. The method of claim 6, wherein each of the plurality of samples comprises at least a portion of a sound of a respective audio file.

10. The method of claim 6, wherein the feature encoder is: (i) a Transformer based feature encoder; (ii) Convolutional Neural Network (CNN) based feature encoder; or (iii) a Recurrent Neural Network (RNN) based feature encoder.

11. The method of claim 6, wherein the neural network generates a similarity measure using one of: (i) a cosine similarity metric; and (ii) a bilinear similarity metric.

12. The method of claim 6, wherein the audio files of the first training set do not include labels indicative of whether the sound of the audio file is a positive example of a condition or a negative example of the condition.

13. The method of claim 6, further comprising deploying the trained feature encoder and the trained classifier on a computing device for use.

14. A non-transient computer-readable storage medium storing instructions that, when executed by a computer, cause the computer to:

a) determine a first training set comprising a plurality of audio files, wherein each audio file comprises a respiratory sound;

b) determine a database comprising a plurality of samples for each of the audio files of the first training set, wherein each sample is associated with an identifier, wherein determining the database comprising the plurality of samples comprises:

i) transforming each audio file into a feature matrix, each feature matrix comprising a first dimension corresponding to a number of frequency bins, and a second dimension corresponding to a number of time frames in the audio file;

ii) for each feature matrix, generating at least one sample, each sample comprising the first dimension corresponding to a number of frequency bins, and a third dimension corresponding to a predefined number of time frames, wherein the third dimension is a subset of the second dimension;

c) determine a batch of sample pairs from the database, wherein the batch comprises one positive sample pair comprising a first sample and second sample, wherein the first sample and the second sample are associated with a common identifier, and the batch comprises a plurality of negative sample pairs, each negative sample pair comprising the first sample and a respective third sample, wherein the identifier associated with each respective third sample is different to the identifier associated with the first sample;

d) apply a first masking matrix having a first masking rate to the first sample to mask one or more select elements of the first sample in accordance with the first masking rate;

e) provide the masked first sample to a feature encoder to generate a first numerical representation of the masked first sample;

f) apply a second masking matrix having a second masking rate to the second sample to mask one or more select elements of the second sample in accordance with the second masking rate;

g) provide the masked second sample of the positive candidate pair to the feature encoder to generate a second numerical representation of the masked second sample;

h) provide the first numerical representation and the second numerical representation to a neural network to generate a first similarity measure indicative of the similarity between the masked first and second samples of the positive candidate pair;

i) determine a plurality of second similarity measures, each second similarity measure being indicative of the similarity between the first and third samples of each of the negative sample pairs, wherein said determining comprises:

for each negative sample pair:

i) applying a third masking matrix having a third masking rate to the third sample to mask one or more select elements of the third sample in accordance with the third masking rate;

ii) providing the masked third sample to the feature encoder to generate a third numerical representation of the masked third sample; and iii) providing the first numerical representation and the third numerical representation to the neural network to generate a second similarity measure between the first and third samples;

j) determine a loss function value using a loss function based on the first similarity measure, and the plurality of second similarity measures;

k) adjust one or more of the weights of the feature encoder based on the determined loss function value;

l) Responsive to an iteration count being less than a threshold value:

i) increment the iteration count; and ii) repeat steps c) to k);

m) responsive to the iteration count reaching the threshold value, determine the feature encoder as a pre-trained feature encoder.

15. The non-transient computer-readable storage medium of claim 14, storing instructions that, when executed by a computer, cause the computer to:

a) determine a second training set of a plurality of audio files, each audio file comprising a label indicative of whether the sound is a positive example of a condition or a negative example of the condition;

b) generate a batch of samples from the second training set, wherein each sample is generated from a respective audio file and is associated with the label of the audio file from which it was generated; and c) for each of the plurality of samples of the second batch:

i) select a candidate sample from the second batch;

ii) provide the candidate sample to the pre-trained feature encoder to generate a candidate numerical representation of the candidate sample;

iii) provide the candidate numerical representation to a classifier to determine a predictive score, wherein the predictive score is indicative of the candidate sample being a positive example of the condition; and iv) adjust one or more weights of the classifier based on the label associated with the candidate sample and the predictive score.

16. The non-transient computer-readable storage medium of claim 15, wherein the pre-trained feature encoder comprises a first pre-trained feature encoder and a second pre-trained feature encoder, and wherein providing the candidate sample to the pre-trained feature encoder comprises:

a) applying a fourth masking matrix having a fourth masking rate to the candidate sample to mask one or more select elements of the candidate sample in accordance with the fourth masking rate to provide a fourth masked sample;

b) applying a fifth masking matrix having a fifth masking rate to the candidate sample to mask one or more select elements of the candidate sample in accordance with the fifth masking rate to provide a fifth masked sample; and c) providing the fourth masked sample to the first pre-trained encoder to generate a fourth numerical representation of the fourth masked sample and providing the fifth masked sample to the second pre-trained encoder to generate a fifth numerical representation of the fifth masked sample; and wherein providing the candidate numerical representation to the classifier comprises providing both the fourth numerical representation and the fifth numerical representation as inputs to the classifier.

17. The non-transient computer-readable storage medium of claim 14, wherein the audio files of the first training set do not include labels indicative of whether the sound of the audio file is a positive example of a condition or a negative example of the condition.

* * * * *